US012569832B2

(12) United States Patent
Koike et al.

(10) Patent No.: US 12,569,832 B2
(45) Date of Patent: Mar. 10, 2026

(54) COMPOSITION FOR CATALYST PRODUCTION, METHOD FOR PRODUCING COMPOSITION FOR CATALYST PRODUCTION, AND PRODUCTION METHOD FOR PRODUCING OXIDE CATALYST

(71) Applicant: ASAHI KASEI KABUSHIKI KAISHA, Tokyo (JP)

(72) Inventors: Natsume Koike, Tokyo (JP); Gosuke Oyama, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 652 days.

(21) Appl. No.: 17/796,571

(22) PCT Filed: Jan. 7, 2021

(86) PCT No.: PCT/JP2021/000287
§ 371 (c)(1),
(2) Date: Jul. 29, 2022

(87) PCT Pub. No.: WO2021/153174
PCT Pub. Date: Aug. 5, 2021

(65) Prior Publication Data

US 2023/0057028 A1 Feb. 23, 2023

(30) Foreign Application Priority Data

Jan. 31, 2020 (JP) ................................ 2020-014597

(51) Int. Cl.
*B01J 23/20* (2006.01)
*B01J 35/40* (2024.01)
(Continued)

(52) U.S. Cl.
CPC ............... *B01J 23/20* (2013.01); *B01J 35/40* (2024.01); *B01J 35/51* (2024.01); *B01J 37/0045* (2013.01); *B01J 37/04* (2013.01); *C07C 253/24* (2013.01)

(58) Field of Classification Search
CPC ........ B01J 23/20; B01J 37/0045; B01J 37/04; C07C 253/24
See application file for complete search history.

(56) References Cited

U.S. PATENT DOCUMENTS 7,498,463 B2 * 3/2009 Hinago .................... B01J 23/20 562/549
2003/0017944 A1 1/2003 Hinago et al.
(Continued)

FOREIGN PATENT DOCUMENTS

CN 101405079 A 4/2009
CN 101616732 A 12/2009
(Continued)

OTHER PUBLICATIONS

English translation of International Preliminary Report on Patentability and Written Opinion mailed Aug. 11, 2022, in PCT/JP2021/000287.

(Continued)

*Primary Examiner* — Anthony J Zimmer
*Assistant Examiner* — Annette Phan
(74) *Attorney, Agent, or Firm* — Birch, Stewart, Kolasch & Birch, LLP

(57) ABSTRACT

Provided is a composition for catalyst production which is used in the production of a catalyst for gas phase catalytic oxidation reaction or a catalyst for gas phase catalytic ammoxidation reaction, wherein the composition for catalyst production is an aqueous solution containing a niobium compound and hydrogen peroxide and optionally containing
(Continued)

an organic acid, a molar ratio (organic acid/Nb) of a concentration of the organic acid to a Nb concentration is 0.00 or more and 2.00 or less, and a molar ratio (hydrogen peroxide/Nb) of a concentration of the hydrogen peroxide to a Nb concentration is 0.01 or more and 50 or less.

9 Claims, 1 Drawing Sheet

(51) Int. Cl.

| | |
|---|---|
| ***B01J 35/51*** | (2024.01) |
| ***B01J 37/00*** | (2006.01) |
| ***B01J 37/04*** | (2006.01) |
| ***C07C 253/24*** | (2006.01) |

(56) References Cited

U.S. PATENT DOCUMENTS

| | | | |
|---|---|---|---|
| 2006/0235238 | A1 | 10/2006 | Komada et al. |
| 2008/0103326 | A1 | 5/2008 | Rosen et al. |
| 2008/0249328 | A1 | 10/2008 | Kaduk et al. |
| 2010/0240921 | A1 | 9/2010 | Tateno et al. |
| 2010/0286432 | A1 | 11/2010 | Tateno et al. |
| 2011/0218352 | A1 | 9/2011 | Besecker et al. |
| 2011/0237821 | A1 | 9/2011 | Brazdil et al. |
| 2013/0053596 | A1 | 2/2013 | Kato et al. |
| 2013/0310593 | A1 | 11/2013 | Ishii et al. |
| 2015/0231604 | A1 | 8/2015 | Ishii et al. |
| 2016/0297753 | A1 | 10/2016 | Ishii et al. |
| 2016/0354761 | A1 | 12/2016 | Ishii et al. |
| 2018/0085737 | A1 | 3/2018 | Miike et al. |
| 2019/0232270 | A1 | 8/2019 | Tateno et al. |

FOREIGN PATENT DOCUMENTS

| | | | |
|---|---|---|---|
| CN | 101909745 | A | 12/2010 |
| EP | 2 179 790 | A1 | 4/2010 |
| EP | 2 902 105 | A1 | 8/2015 |
| EP | 2 913 104 | A1 | 9/2015 |
| JP | 11-57479 | A | 3/1999 |
| JP | 2006-55681 | A | 3/2006 |
| JP | 2007-216081 | A | 8/2007 |
| JP | 2011-529777 | A | 12/2011 |
| JP | 2017-29884 | A | 2/2017 |
| JP | 2017-51934 | A | 3/2017 |
| KR | 10-2016-0011830 | A | 2/2016 |
| RU | 2 600 977 | C2 | 10/2016 |
| TW | 201811434 | A | 4/2018 |
| WO | WO 2008/103255 | A1 | 8/2008 |
| WO | WO 2012/105543 | A1 | 8/2012 |
| WO | WO 2014/050615 | A1 | 4/2014 |

OTHER PUBLICATIONS

Supplementary European Search Report for corresponding European Application No. 21748195.1, dated Jun. 20, 2023.

International Search Report (PCT/ISA/210) issued in PCT/JP2021/000287, dated Mar. 30, 2021.

Written Opinion of the International Searching Authority (PCT/ISA/237) issued in PCT/JP2021/000287, dated Mar. 30, 2021.

* cited by examiner

Aqueous Nb solution containing only organic acid
Comparative Example 2
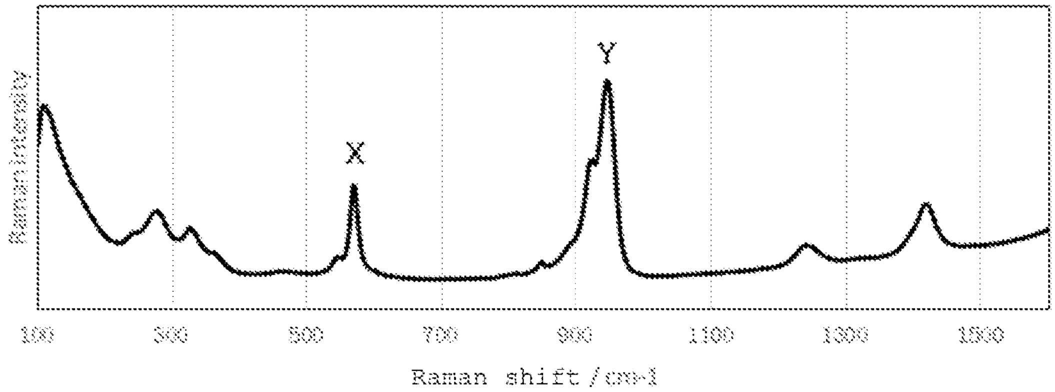
Aqueous Nb solution containing hydrogen peroxide
Example 4
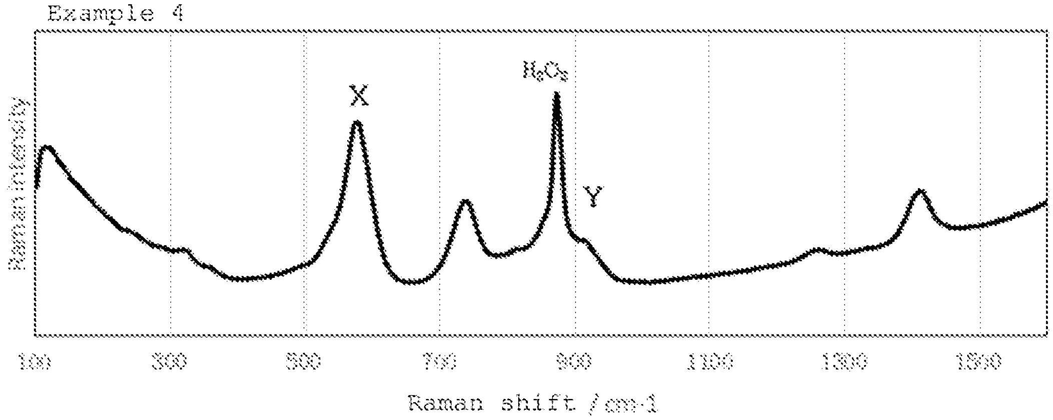

COMPOSITION FOR CATALYST PRODUCTION, METHOD FOR PRODUCING COMPOSITION FOR CATALYST PRODUCTION, AND PRODUCTION METHOD FOR PRODUCING OXIDE CATALYST

TECHNICAL FIELD

The present invention relates to a composition for catalyst production, a method for producing a composition for catalyst production, and a production method for producing an oxide catalyst.

BACKGROUND ART

Composite metal oxide containing a plurality of metals such as molybdenum and vanadium has heretofore been utilized as a catalyst for use in producing acrylonitrile. Examples of a general method for producing such a composite metal oxide catalyst include a method comprising the steps of preparing a slurry containing metal salts constituting the catalyst, and spray-drying and calcining the slurry. In this respect, if the slurry containing metal salts is heterogeneous, the resulting catalyst is also heterogeneous. Therefore, composite metal oxide having the desired composition cannot be obtained. Thus, it is desired to prepare a slurry containing uniformly dissolved metal salts.

Such a metal salt exhibits poor solubility depending on a metal species in the metal salt. For obtaining composite metal oxide from the slurry, it is necessary to sufficiently dissolve this poorly soluble metal salt. Among the metals that are used as starting materials for the catalyst, for example, niobium (Nb) is known to form a backbone serving as an active site in the catalyst, and to also contribute to the suppression of degradation of a product, etc. when the catalyst containing niobium is used in reaction. Inexpensive and stable niobium oxide ($Nb_2O_5$) is generally used as a Nb source in the starting materials for the catalyst. However, since $Nb_2O_5$ is poorly soluble in water, a homogeneous slurry is difficult to obtain when $Nb_2O_5$ in an amount that can sufficiently enhance catalyst performance is added to the slurry of the starting materials for the catalyst. Accordingly, studies have been made on methods for obtaining a homogeneous slurry containing niobium for the production of the composite metal oxide catalyst.

For example, Patent Literature 1 discloses a method for preparing a niobium compound-containing aqueous solution by using a production apparatus comprising: an anticorrosive mixing vessel provided with a stirring unit, a heating unit, and a cooling unit; and a filter for filtering an undissolved Nb compound and deposited dicarboxylic acid, wherein filtration is performed under pressure. The method of Patent Literature 1 employs an approach of heating $Nb_2O_5$ together with an aqueous solution containing carboxylic acid such as oxalic acid as a chelating agent so that a niobium oxalate complex is formed to obtain an aqueous niobium oxalate complex solution, and obtaining a slurry from the aqueous niobium oxalate complex solution. According to the method of Patent Literature 1, residues of an undissolved Nb compound or deposits can be reduced in the resulting aqueous mixed solution of the Nb compound and dicarboxylic acid, and the rate of Nb recovery and the productivity of the mixed solution are reportedly enhanced.

CITATION LIST

Patent Literature

Patent Literature 1: International Publication No. WO 2012/105543

SUMMARY OF INVENTION

Technical Problem

In Patent Literature 1, the aqueous mixed solution of a solid niobium starting material and oxalic acid, which can be used in catalyst production, is obtained, as mentioned above, as an aqueous niobium oxalate complex solution by heating the solid niobium starting material $Nb_2O_5$ together with an aqueous solution containing an acid substance such as oxalic acid as a chelating agent so that a Nb oxalate complex is formed. In this context, the oxalic acid acts as a reducing agent and therefore might over-reduce a composite metal oxide catalyst obtained from the aqueous solution, leading to concerns for reduced catalytic activity. Thus, it is necessary to minimize the amount of the oxalic acid used. However, a reduced amount of the oxalic acid used based on the amount of niobium incurs reduction in the solubility of the Nb compound.

In Patent Literature 1, specifically, an aqueous solution containing oxalic acid is first prepared with heating, and $Nb_2O_5$ is added thereto, followed by stirring with heating to obtain an aqueous mixed solution. Next, this aqueous mixed solution is allowed to cool naturally, left standing, further cooled, and left standing, and an excess of oxalic acid is deposited as a solid through these steps. Further, the deposited solid is filtered off to obtain an aqueous niobium oxalate complex solution.

Although the method described above can remove an excess of oxalic acid, the aqueous Nb oxalate complex solution still contains oxalic acid in a saturated state at a temperature of the cooling step and, unfortunately, fails to sufficiently remove unnecessary oxalic acid. Furthermore, oxalic acid to be removed as a solid is discarded. Therefore, it is desired to reduce the amount of oxalic acid used from the viewpoint of cost reduction and reduction of environmental burdens and also because the oxalic acid is poisonous.

The process of producing the aqueous Nb oxalate complex solution involves cooling and solid removal steps and is thus complicated. Therefore, there is a demand for methods for conveniently obtaining such an aqueous niobium oxalate complex solution.

Accordingly, an object of the present invention is to provide a composition for catalyst production with a reduced amount of an acid substance such as oxalic acid used despite containing a niobium compound, a production method that can efficiently obtain the composition for catalyst production, and a production method for producing an oxide catalyst using the composition for catalyst production.

Solution to Problem

The present inventors have conducted diligent studies to attain the object and consequently completed the present invention by finding that use of a solid niobium starting material and hydrogen peroxide efficiently produces an aqueous solution containing a niobium compound while reducing the amount of an acid substance such as oxalic acid used.

Specifically, the present invention encompasses the following aspects.

[1]

A composition for catalyst production which is used in the production of a catalyst for gas phase catalytic oxidation reaction or a catalyst for gas phase catalytic ammoxidation reaction, wherein the composition for catalyst production is an aqueous solution comprising a niobium compound and hydrogen peroxide and optionally comprising an organic acid, a molar ratio (organic acid/Nb) of a concentration of the organic acid to a Nb concentration in the composition for catalyst production is 0.00 or more and 2.00 or less, and a molar ratio (hydrogen peroxide/Nb) of a concentration of the hydrogen peroxide to a Nb concentration in the composition for catalyst production is 0.01 or more and 50 or less.

[2]

The composition for catalyst production according to [1], wherein the organic acid is one or more carboxylic acid compounds selected from the group consisting of dicarboxylic acid, dicarboxylic anhydride, dicarboxylic acid hydrate, and oxycarboxylic acid.

[3]

The composition for catalyst production according to [1] or [2], wherein in a Raman spectrum of the composition for catalyst production by Raman spectroscopy, a ratio (Y/X) of intensity Y of the largest peak observed in the range of 890 $cm^{-1}$ or more and 1000 $cm^{-1}$ or less to intensity X of the largest peak observed in the range of 500 $cm^{-1}$ or more and 650 $cm^{-1}$ or less is 0 or more and 1.0 or less.

[4]

The composition for catalyst production according to any one of [1] to [3], wherein in a Raman spectrum of the composition for catalyst production by Raman spectroscopy, a peak is present in the range of 685 $cm^{-1}$ or more and 785 $cm^{-1}$ or less.

[5]

A composition for catalyst production which is used in the production of a catalyst for gas phase catalytic oxidation reaction or a catalyst for gas phase catalytic ammoxidation reaction, wherein the composition for catalyst production is an aqueous solution comprising a niobium compound and hydrogen peroxide and optionally comprising an organic acid, and in a Raman spectrum of the composition for catalyst production by Raman spectroscopy, a ratio (Y/X) of intensity Y of the largest peak observed in the range of 890 $cm^{-1}$ or more and 1000 $cm^{-1}$ or less to intensity X of the largest peak observed in the range of 500 $cm^{-1}$ or more and 650 $cm^{-1}$ or less is 0 or more and 1.0 or less.

[6]

The composition for catalyst production according to [5], wherein a molar ratio (organic acid/Nb) of a concentration of the organic acid to a Nb concentration in the composition for catalyst production is 0.00 or more and 2.00 or less, and a molar ratio (hydrogen peroxide/Nb) of a concentration of the hydrogen peroxide to a Nb concentration in the composition for catalyst production is 0.01 or more and 50 or less.

[7]

A method for producing a catalyst for gas phase catalytic oxidation reaction or a catalyst for gas phase catalytic ammoxidation reaction which is used in the production of an unsaturated acid or unsaturated nitrile, the oxide catalyst production method comprising:

a step of preparing an aqueous mixed solution comprising a Mo starting material, a V starting material and a Sb starting material;

a step of mixing a composition for catalyst production according to any one of [1] to [6] with the aqueous mixed solution to prepare a precursor slurry;

a drying step of drying the precursor slurry to obtain dried particles; and a calcination step of calcining the dried particles to obtain calcined particles.

[8]

A method for producing a composition for catalyst production which is used in the production of a catalyst for gas phase catalytic oxidation reaction or a catalyst for gas phase catalytic ammoxidation reaction, comprising:

a mixing step of mixing a solid niobium starting material and hydrogen peroxide water to prepare a dispersion of the solid niobium starting material; and a dissolution step of dissolving the solid niobium starting material in the dispersion of the solid niobium starting material to prepare a niobium compound-containing aqueous solution, wherein a molar ratio (hydrogen peroxide/Nb) of a concentration of hydrogen peroxide to a Nb concentration of the niobium compound in the niobium compound-containing aqueous solution is 0.01 or more and 50 or less, and a temperature of the dissolution step is 40° C. or higher and 70° C. or lower.

[9]

The method for producing a composition for catalyst production according to [8], wherein in the mixing step, an organic acid is further mixed, and a molar ratio (organic acid/Nb) of a concentration of the organic acid to a Nb concentration of the niobium compound in the niobium compound-containing aqueous solution is 0.00 or more and 2.00 or less.

[10]

The method for producing a composition for catalyst production according to [8] or [9], wherein the solid niobium starting material contains niobic acid.

[11]

The method for producing a composition for catalyst production according to any one of [8] to [10], wherein the organic acid includes one or more carboxylic acid compounds selected from the group consisting of dicarboxylic acid, dicarboxylic anhydride, dicarboxylic acid hydrate, and oxycarboxylic acid.

[12]

A method for producing a catalyst for gas phase catalytic oxidation reaction or a catalyst for gas phase catalytic ammoxidation reaction which is used in the production of an unsaturated acid or unsaturated nitrile, comprising:

a step of using a method for producing a composition for catalyst production according to any one of [8] to [11] to prepare the composition for catalyst production;

- a step of preparing an aqueous mixed solution comprising a Mo starting material, a V starting material and a Sb starting material;
- a step of mixing the composition for catalyst production with the aqueous mixed solution to prepare a precursor slurry;
- a drying step of drying the precursor slurry to obtain dried particles; and
- a calcination step of calcining the dried particles to obtain calcined particles.

Advantageous Effects of Invention

The present invention can provide a composition for catalyst production with a reduced amount of an acid substance such as oxalic acid used despite containing a niobium compound, a production method that can efficiently obtain the composition for catalyst production, and a production method for producing an oxide catalyst using the composition for catalyst production.

BRIEF DESCRIPTION OF DRAWING

[FIG. 1] The upper diagram shows a Raman spectrum of a niobium compound-containing aqueous solution containing an organic acid (oxalic acid) without the use of hydrogen peroxide (composition for catalyst production according to Comparative Example 2) by Raman spectroscopy. The lower diagram shows a Raman spectrum of a niobium compound-containing aqueous solution containing hydrogen peroxide and an organic acid (oxalic acid) (composition for catalyst production according to Example 4) by Raman spectroscopy.

DESCRIPTION OF EMBODIMENTS

Hereinafter, the mode for carrying out the present invention (hereinafter, referred to as the "present embodiment") will be described in detail. The present invention is not limited by the following present embodiment, and various changes or modifications can be made therein without departing from the spirit of the present invention.

Method for Producing Composition for Catalyst Production

The method for producing a composition for catalyst production according to the present embodiment is a method for producing a composition for catalyst production which is used in the production of a catalyst for gas phase catalytic oxidation reaction or a catalyst for gas phase catalytic ammoxidation reaction, comprising: a mixing step of mixing a solid niobium starting material and hydrogen peroxide to prepare a dispersion of the solid niobium starting material; and a dissolution step of dissolving the solid niobium starting material in the dispersion of the solid niobium starting material to prepare an aqueous solution containing a niobium compound (hereinafter, also referred to as a niobium compound-containing aqueous solution), wherein a molar ratio (hydrogen peroxide/Nb) of a concentration of hydrogen peroxide to a Nb concentration in the niobium compound-containing aqueous solution is 0.01 or more and 50 or less, and a temperature of the dissolution step is 40° C. or higher and 70° C. or lower.

The composition for catalyst production according to the present embodiment refers to a composition as a material for preparing a catalyst for gas phase catalytic oxidation reaction or a catalyst for gas phase catalytic ammoxidation reaction, and is an aqueous solution containing a niobium compound which is obtained by the steps described above.

In this context, the "solid niobium starting material" used herein means a solid of a niobium starting material such as a powdery niobium starting material before mixing with an aqueous hydrogen peroxide solution in obtaining the composition for catalyst production. The "dispersion of the solid niobium starting material" is a dispersion in a merely mixed state of the solid niobium starting material and hydrogen peroxide and refers to a state before dissolution of the solid niobium starting material in hydrogen peroxide water.

The "niobium compound" means a niobium starting material in a dissolved state of the solid niobium starting material in the niobium compound-containing aqueous solution or the composition for catalyst production. Examples thereof include niobium-hydrogen peroxide-oxalic acid complexes, niobium-hydrogen peroxide complexes, niobium-oxalic acid complexes and aggregates containing two or more of these complexes.

In the production method of the present embodiment, an aqueous solution containing a niobium compound is obtained from a solid niobium starting material and hydrogen peroxide. The aqueous solution containing a niobium compound can be obtained, without the use of an excess of an acid substance such as oxalic acid, by preparing the niobium compound-containing aqueous solution using hydrogen peroxide water. Furthermore, the production method of the present embodiment can omit a step of depositing and removing a redundant acid substance, which has heretofore been performed in the preparation of the niobium compound-containing aqueous solution. Thus, the production method of the present embodiment enables the niobium compound-containing aqueous solution to be efficiently obtained without the use of an excess of an acid substance.

The solid niobium starting material is not particularly limited as long as the compound contains a niobium element. Examples of the solid niobium starting material can include, but are not limited to, niobium binoxalate, niobium ammonium oxalate, $NbCl_3$, $NbCl_5$, $Nb_2(C_2O_4)_5$, niobium oxide (also referred to as $Nb_2O_5$), niobic acid, $Nb(OC_2H_5)_5$, niobium halide, and ammonium halide of niobium. One of these compounds may be used singly, or two or more thereof may be used in combination.

Among them, $Nb_2O_5$, niobic acid and niobium binoxalate are preferred from the viewpoint of reducing influence on other metals when the metals are added to the composition for catalyst production. The niobic acid may contain niobium hydroxide and niobium oxide ($Nb_2O_5$). The solid niobium starting material may be used immediately after production of the solid niobium starting material, or may contain a solid niobium starting material altered due to long-term preservation or the progression of dehydration.

In preparing the composition for catalyst production, the solid niobium starting material may be a solid or may be in the form of a suspension. In the case of using, for example, niobic acid, niobic acid having a small particle size is preferred from the viewpoint of more improving solubility. The niobic acid may be washed with ammonia water and/or water before use.

In the production method of the present embodiment, the particle size of the solid niobium starting material is preferably 0.2 μm or larger and 20 μm or smaller. The particle size of 0.2 μm or larger increases the tackiness among fine particles of the solid niobium starting material and suppresses the surface drying of the solid niobium starting material. Therefore, solubility tends to be enhanced. The particle size of 20 μm or smaller increases the surface area of the solid niobium starting material. Therefore, solubility tends to be enhanced. The particle size of the solid niobium starting material is more preferably 0.7 μm or larger and 15.0 μm or smaller, further preferably 2.0 μm or larger and 10.0 μm or smaller.

In the production method of the present embodiment, the molar ratio (hydrogen peroxide/Nb) of the concentration of hydrogen peroxide to the Nb concentration in the niobium compound-containing aqueous solution is 0.01 or more and 50 or less, preferably 0.5 or more and 10 or less. The molar ratio (hydrogen peroxide/Nb) of 0.01 or more tends to enhance the solubility of the solid niobium starting material in water. The molar ratio (hydrogen peroxide/Nb) of 50 or less tends to enhance the solubility without influencing the functionality of the resulting catalyst.

The lower limit of the molar ratio (hydrogen peroxide/Nb) is preferably 0.5 or more, more preferably 1.0 or more, further preferably 2.0 or more. On the other hand, the upper limit of the molar ratio (hydrogen peroxide/Nb) is preferably 45.0 or less, more preferably 30.0 or less.

In the production method of the present embodiment, an organic acid may be further added in obtaining the niobium compound-containing aqueous solution. Thus, one embodiment of the present invention provides the production method further comprising mixing an organic acid in the step of obtaining a niobium compound-containing aqueous solution. The organic acid mixed into the niobium compound-containing aqueous solution tends to further enhance the solubility of the solid niobium starting material in water.

Examples of the organic acid according to the present embodiment can include, but are not particularly limited to, one or more carboxylic acid compounds selected from the group consisting of dicarboxylic acid, dicarboxylic anhydride, dicarboxylic acid hydrate, and oxycarboxylic acid. Examples of the dicarboxylic acid include oxalic acid, malonic acid, succinic acid, and glutaric acid. One of these acids may be used singly, or two or more thereof may be used in combination. Among them, oxalic acid is preferred from the viewpoint of suppressing the over-reduction of metal oxide in catalyst production. The oxalic acid is preferably oxalic anhydride or oxalic acid dihydrate.

The oxycarboxylic acid is a compound having a hydroxy group and a carboxyl group in one molecule. Examples of the oxycarboxylic acid include 2-hydroxymalonic acid, DL-malic acid, L-malic acid, D-malic acid, tartaric acid, citric acid, and isocitric acid.

In the production method of the present embodiment, in the case of preparing a dispersion of the solid niobium starting material containing an organic acid, the upper limit of the molar ratio (organic acid/Nb) of the amount of the organic acid added to the Nb concentration in the niobium compound-containing aqueous solution is not particularly limited and is preferably 2.50 or less, more preferably 2.30 or less, further preferably 2.00 or less, still further preferably 1.80 or less, even further preferably 1.50 or less, particularly preferably 1.00 or less. On the other hand, the lower limit of the molar ratio (organic acid/Nb) is 0.00 or more. The molar ratio (organic acid/Nb) of 0.00, i.e., 0, means that the organic acid is not added.

In the production method of the present embodiment, the amount of an organic acid such as oxalic acid used, which acts as a reducing agent, can be reduced. A composite metal oxide catalyst obtained from the niobium compound-containing aqueous solution with a reduced amount of oxalic acid, etc. is prevented from falling into an over-reduced state, and has enhanced catalytic activity, probably contributing to improvement in the yield of a reaction product. Thus, particularly, in the case of using, for example, an organic acid, such as oxalic acid, which acts as a reducing agent, a reduced content of the organic acid enhances the activity of a composite metal oxide catalyst obtained from the niobium compound-containing aqueous solution, and tends to be able to improve the yield of a reaction product.

The production method of the present embodiment comprises a mixing step of mixing a solid niobium starting material and hydrogen peroxide to prepare a dispersion of the solid niobium starting material. In the mixing step, an organic acid is added, if necessary, and a dispersion of the solid niobium starting material containing the organic acid may be prepared. The temperature of the mixing step is not particularly limited and is usually ordinary temperature or may be 40° C. or higher and 70° C. or lower, as in the temperature of a dissolution step mentioned later. The "ordinary temperature" used herein means a temperature in a range on the order of 15° C. or higher and 25° C. or lower.

The production method of the present embodiment comprises a dissolution step of mixing and dissolving the solid niobium starting material, hydrogen peroxide, water, and optionally the organic acid under a condition of 40° C. or higher and 70° C. or lower in order to obtain a niobium compound-containing aqueous solution. The temperature of 40° C. or higher tends to promote the dissolution of the solid niobium starting material. The temperature of 70° C. or lower tends to suppress the degradation of hydrogen peroxide. Furthermore, when the mixture contains an additive such as the organic acid, a complex of the organic acid and Nb to be formed in the composition for catalyst production is stabilized. Thus, sufficient dispersibility tends to be more secured even if Nb has a high concentration. The temperature is more preferably 60° C. or lower.

In the dissolution step according to the present embodiment, the heating method is not particularly limited. At the time of heating, it is preferred to perform stirring together with the heating.

In the production method of the present embodiment, it is desired to take a sufficient time after mixing from the viewpoint of sufficiently dissolving the solid niobium starting material. The dissolution step is preferably carried out for 0.2 hours or longer and 20 hours or shorter, more preferably for 0.3 hours or longer and 15 hours or shorter, further preferably for 0.5 hours or longer and 10 hours or shorter, from the viewpoint of securing sufficient dispersibility even when the niobium compound-containing aqueous solution has a high Nb concentration.

The temperature of water for use in the mixing step according to the present embodiment is not particularly limited and is preferably 10° C. or higher and 50° C. or lower. The water temperature of 10° C. or higher tends to more facilitate the dissolution of the solid niobium starting material in the dissolution step. The water temperature of 50° C. or lower can prevent the periphery of an injection port from being wettened by water vapor and permits easy injection of the solid niobium starting material.

The temperatures of the solid niobium starting material, hydrogen peroxide, and optionally the organic acid to be added are not particularly limited, and these components are preferably added at 50° C. or lower for the same reasons as above.

The production method of the present embodiment is not particularly limited as long as the niobium compound-containing aqueous solution is obtained. The solid niobium starting material, hydrogen peroxide, water, and optionally the organic acid can be blended in an arbitrary order.

The solid niobium starting material and hydrogen peroxide, and optionally the organic acid are preferably added with stirring to a system containing water from the viewpoint of preventing the solid niobium starting material from being left undissolved. Then, the temperature of the resulting mixture is preferably increased to the range of 40° C. or higher and 70° C. or lower. The temperature increase speed is not particularly limited and can be usually 1° C./hr or more and 60° C./hr or less.

In the case of performing heating to higher than 40° C., the temperature of the mixture thus heated is preferably decreased to 40° C. or lower. In this respect, the temperature decrease speed is preferably 0.002° C./min or more and 3° C./min or less. The temperature decrease speed of 0.002° C./min or more tends to be able to suppress the redeposition of niobium. The temperature decrease speed of 3° C./min or less can prevent the deposition of niobium attributed to rapid temperature decrease and tends to obtain a homogeneous solution.

In the production method of the present embodiment, the niobium compound-containing aqueous solution obtained by mixing the solid niobium starting material, hydrogen peroxide, and water may be used as the composition for catalyst production, or a Nb-containing mixture obtained by mixing the solid niobium starting material, hydrogen peroxide, and water may be supplied to a filter, followed by filtration, and the obtained niobium compound-containing aqueous solution may be used as the composition for catalyst production. Specifically, the production method preferably comprises a step of supplying the Nb-containing mixture to a filter, followed by filtration. This can remove solid matter such as undissolved matter of niobium, undissolved matter of the organic acid, or deposits in the mixture. A filter paper of No. 5A or finer may be appropriately used. For example, A No. 3250 manufactured by Azumi Filter Paper can be used. In the filtration step, the mixture is preferably filtered at a rate of 1 kg/hr or more and 100 kg/hr or less so that deposits are filtered off to obtain a homogeneous solution. During filtration, cooling water may be applied to a jacket disposed on the outer side of the filter in order to keep the filtrate temperature constant.

In the production method of the present embodiment, the solid niobium starting material is preferably added such that the Nb concentration of the niobium compound-containing aqueous solution is 0.10 mol/kg or higher. The Nb concentration of 0.10 mol/kg or higher tends to secure a Nb concentration sufficient for the composition for catalyst production. The Nb concentration is preferably 1.00 mol/kg or lower from the viewpoint of suppressing the deposition of niobium in the niobium compound-containing aqueous solution and improving preservability. From such a viewpoint, the Nb concentration is more preferably 0.20 mol/kg or higher and 1.00 mol/kg or lower, further preferably 0.20 mol/kg or higher and 0.70 mol/kg or lower.

In the production method of the present embodiment, the hydrogen peroxide concentration ($H_2O_2$ concentration) of the niobium compound-containing aqueous solution is not particularly limited as long as the molar ratio (hydrogen peroxide/Nb) is satisfied. The concentration is usually 0.3 mol/kg or higher and 9.0 mol/kg or lower. The upper limit of the hydrogen peroxide concentration of the niobium compound-containing aqueous solution is preferably 10.0 mol/kg or lower, more preferably 9.0 mol/kg or lower. On the other hand, the lower limit of the hydrogen peroxide concentration is preferably 0.2 mol/kg or higher, more preferably 0.3 mol/kg or higher.

Composition for Catalyst Production

As mentioned above, the present inventors have found that use of hydrogen peroxide water in the production of a niobium compound-containing aqueous solution produces the niobium compound-containing aqueous solution by dissolving the solid niobium starting material without the use of an organic acid, and successfully obtained, for the first time, an aqueous solution containing a niobium compound with a reduced amount of an acid substance such as an organic acid used.

Use of hydrogen peroxide in preparing the niobium compound-containing aqueous solution can increase the Nb concentration of the aqueous solution while decreasing an organic acid/Nb ratio to 2.00 or less.

Thus, a composition for catalyst production of the present embodiment is a composition for catalyst production which is used in the production of a catalyst for gas phase catalytic oxidation reaction or a catalyst for gas phase catalytic ammoxidation reaction, wherein the composition for catalyst production is an aqueous solution containing a niobium compound and hydrogen peroxide and optionally containing an organic acid, a molar ratio (organic acid/Nb) of an amount of the organic acid to a Nb concentration in the composition for catalyst production is 0.00 or more and 2.00 or less, and a molar ratio (hydrogen peroxide/Nb) of a concentration of the hydrogen peroxide to a Nb concentration in the composition for catalyst production is 0.01 or more and 50 or less.

The molar ratio (organic acid/Nb) in the composition for catalyst production of the present embodiment is preferably 1.80 or less, more preferably 1.50 or less, further preferably 1.00 or less, particularly preferably less than 1.00. The lower limit of the molar ratio (organic acid/Nb) is 0.00 or more. The molar ratio (organic acid/Nb) of 0.00 is meant to include the case where the content of the organic acid is 0. The molar ratio (organic acid/Nb) of 2.00 or less tends to obtain an aqueous solution containing Nb while reducing the amount of the organic acid.

The molar ratio (organic acid/Nb) and the molar ratio (hydrogen peroxide/Nb) in the composition for catalyst production of the present embodiment are each calculated on the basis of the Nb concentration, the organic acid concentration (Ox concentration) and the hydrogen peroxide concentration ($H_2O_2$ concentration) of the composition for catalyst production. The respective concentrations can be measured using the composition after a lapse of an arbitrary time from its preparation, and is measured, for example, after the composition is left standing for 1 day. No significant difference is found in each molar ratio even after the composition is left standing for 1 day.

Each of the concentrations can be specifically measured by a method described in Examples mentioned later.

Examples of a method for setting the molar ratio (organic acid/Nb) to 2.00 or less include a method of adjusting the molar ratio by the method for producing a composition for catalyst production according to the present embodiment mentioned above.

In the composition for catalyst production of the present embodiment, the molar ratio (hydrogen peroxide/Nb) of the concentration of hydrogen peroxide to the Nb concentration is 0.01 or more and 50 or less. The lower limit of the molar ratio (hydrogen peroxide/Nb) is preferably 0.5 or more, more preferably 1.0 or more, further preferably 2.0 or more. On the other hand, the upper limit of the molar ratio (hydrogen peroxide/Nb) is preferably 45.0 or less, more preferably 30.0 or less. The molar ratio (hydrogen peroxide/Nb) of 0.01 or more tends to obtain an aqueous solution containing Nb while reducing the amount of the organic acid. The molar ratio (hydrogen peroxide/Nb) of 50 or less tends to enhance solubility without influencing the functionality of a catalyst obtained by catalyst production.

In the composition for catalyst production of the present embodiment, the Nb concentration is not particularly limited as long as the molar ratio (organic acid/Nb) and the molar ratio (hydrogen peroxide/Nb) are satisfied. The concentration is usually 0.2 mol/kg or higher and 1.0 mol/kg or lower. The upper limit of the Nb concentration of the composition for catalyst production is preferably 1.2 mol/kg or lower, more preferably 1.0 mol/kg or lower. On the other hand, the lower limit of the Nb concentration is preferably 0.1 mol/kg or higher, more preferably 0.2 mol/kg or higher.

In the composition for catalyst production of the present embodiment, the hydrogen peroxide concentration ($H_2O_2$ concentration) is not particularly limited as long as the molar ratio (hydrogen peroxide/Nb) is satisfied. The concentration is usually 0.3 mol/kg or higher and 9.0 mol/kg or lower. The upper limit of the hydrogen peroxide concentration of the composition for catalyst production is preferably 10.0 mol/kg or lower, more preferably 9.0 mol/kg or lower. On the other hand, the lower limit of the hydrogen peroxide concentration is preferably 0.2 mol/kg or higher, more preferably 0.3 mol/kg or higher.

In the composition for catalyst production of the present embodiment, the organic acid concentration (Ox concentration) is not particularly limited as long as the molar ratio (organic acid/Nb) is satisfied. The concentration is usually 0 mol/kg or higher and 1.5 mol/kg or lower. The upper limit of the organic acid concentration of the composition for catalyst production is preferably 1.6 mol/kg or lower, more preferably 1.5 mol/kg or lower. On the other hand, the lower limit of the organic acid concentration is preferably 0 mol/kg or higher, more preferably 0.1 mol/kg or higher.

For the composition for catalyst production of the present embodiment and the composition for catalyst production obtained by the production method of the present embodiment, the solubility of a solid niobium starting material is enhanced by using hydrogen peroxide in preparing an aqueous solution of the solid niobium starting material. This may be partly because use of hydrogen peroxide forms a complex different from that obtained using only an organic acid and this complex contributes to improvement in solubility.

Examples of the complex to be formed in the present embodiment include complexes represented by the following formulas (I) to (III) (see Inorg. Chem., Vol. 43 (19), 5999, 2004; ACS Catal., vol. 8, 4645, 2018; etc.).

(I)

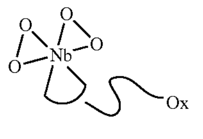

(II)

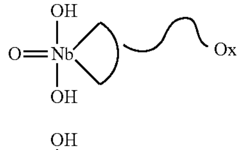

(III)

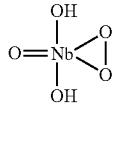

wherein Ox represents a ligand derived from an organic acid.

The structures of the formulas (I) to (III) are defined as follows.

Formula (I): a niobium complex coordinated with one molecule of oxalic acid and two molecules of hydrogen peroxide Formula (II): a niobium complex coordinated with one molecule of oxalic acid Formula (III): a niobium complex coordinated with one molecule of hydrogen peroxide The composition for catalyst production of the present embodiment comprising no organic acid may comprise a complex represented by the formula (III) or a complex having any of other structures. The composition for catalyst production of the present embodiment comprising an organic acid may comprise a complex of at least one of the formulas (I) to (III) or having any of other structures.

In actuality, a Raman spectrum different from that of a complex obtained using only an organic acid is obtained when the composition for catalyst production of the present embodiment and the composition for catalyst production obtained by the production method of the present embodiment are measured by Raman spectroscopy (see FIG. 1). Thus, the measurement of the composition for catalyst production according to the present embodiment by Raman spectroscopy can be a method for identifying the composition for catalyst production of the present embodiment.

From such a viewpoint, a composition for catalyst production of the present embodiment is preferably a composition for catalyst production which is used in the production of a catalyst for gas phase catalytic oxidation reaction or a catalyst for gas phase catalytic ammoxidation reaction, wherein the composition for catalyst production is an aqueous solution containing a niobium compound and hydrogen peroxide and optionally containing an organic acid, and in a Raman spectrum obtained by measuring the composition for catalyst production by Raman spectroscopy, a ratio (Y/X) of intensity Y of the largest peak observed in the range of 890 $cm^{-1}$ or more and 1000 $cm^{-1}$ or less to intensity X of the largest peak observed in the range of 500 $cm^{-1}$ or more and 650 $cm^{-1}$ or less is preferably 0 or more and 1.0 or less.

The ratio (Y/X) of 1.0 or less tends to enhance the solubility of Nb in water. The ratio (Y/X) is preferably 0.8 or less, more preferably 0.6 or less, further preferably 0.4 or less, particularly preferably 0.3 or less. The lower limit of the ratio (X/Y) is not particularly limited and is usually 0.0 or more. The ratio (X/Y) of 0.0 means that a complex obtained using only an organic acid is excluded.

The composition for catalyst production of the present embodiment preferably has a peak in the range of 685 $cm^{-1}$ or more and 785 $cm^{-1}$ or less in its Raman spectrum by Raman spectroscopy. The presence of the peak in the range of 685 $cm^{-1}$ or more and 785 $cm^{-1}$ or less means that the structure of Nb—O—Nb is abundant. The structure of Nb—O—Nb is easily formed in an aqueous solution having a high Nb concentration. This can therefore be confirmed from the peak in the range of 685 $cm^{-1}$ or more and 785 $cm^{-1}$ or less. Further, such an aqueous solution having a high Nb concentration is easily adapted to appropriate conditions in the process of producing a catalyst and is therefore desirable. Particularly, a higher Nb concentration in a drying step renders the shape of produced catalyst particles closer to a spheric shape and more favorable.

The peak of Y corresponds to the vibration of a Nb═O bond formed in Nb coordinated with oxalic acid, and the peak of X corresponds to the vibration of a Nb—O bond, regardless of whether to be coordinated with oxalic acid (see J. Raman. Spec., Vol. 22, 83-89, 1991, etc.).

The composition for catalyst production of the present embodiment may have both of a configuration based on the molar ratio (organic acid/Nb) and the molar ratio (hydrogen peroxide/Nb) and a configuration based on the ratio (Y/X).

Examples of the niobium compound and the organic acid in the composition for catalyst production can include the same as those mentioned about the method for producing a composition for catalyst production.

Method for Producing Catalyst

One embodiment of the present invention provides a method for producing an oxide catalyst for gas phase catalytic oxidation reaction or for gas phase catalytic ammoxidation reaction which is used in the production of an unsaturated acid or unsaturated nitrile. The method for producing an oxide catalyst according to the present embodiment is not particularly limited as long as the method employs the composition for catalyst production of the present embodiment or comprises the steps of the method for producing a composition for catalyst production according to the present embodiment. Specifically, the method for producing an oxide catalyst according to the present embodiment is a method for producing an oxide catalyst which is used in the production of an unsaturated acid or unsaturated nitrile, comprising a step of obtaining the oxide catalyst using the composition for catalyst production of the present embodiment. Alternatively, the method for producing an oxide catalyst according to the present embodiment is a method for producing an oxide catalyst which is used in the production of an unsaturated acid or unsaturated nitrile, comprising the steps of the method for producing a composition for catalyst production according to the present embodiment.

Specifically, the method for producing a catalyst according to the present embodiment preferably comprises: a step of preparing an aqueous mixed solution containing a Mo starting material, a V starting material and a Sb starting material; a step of mixing the composition for catalyst production with an aqueous mixed solution to prepare a precursor slurry; a drying step of drying the precursor slurry to obtain dried particles; and a calcination step of calcining the dried particles to obtain calcined particles.

Alternatively, the method for producing a catalyst according to the present embodiment preferably comprises: a step of preparing a composition for catalyst production by the method for producing a composition for catalyst production according to the present embodiment; a step of preparing an aqueous mixed solution containing a Mo starting material, a V starting material and a Sb starting material; a step of mixing the composition for catalyst production with the aqueous mixed solution to prepare a precursor slurry; a drying step of drying the precursor slurry to obtain dried particles; and a calcination step of calcining the dried particles to obtain calcined particles.

The catalyst obtained by any of these methods is preferably a catalyst for acrylonitrile production containing Mo, V, Sb and Nb. Hereinafter, each step will be described. The step of preparing a composition for catalyst production by the method for producing a composition for catalyst production according to the present embodiment is as mentioned above, so that the description is omitted.

Precursor Slurry Preparation Step

The method for producing a catalyst according to the present embodiment may comprise, as the first step, a precursor slurry preparation step of preparing a precursor slurry containing the composition for catalyst production of the present embodiment and/or a composition for catalyst production obtained by the method for producing a composition for catalyst production according to the present embodiment.

The precursor slurry preparation step comprises the steps of: preparing an aqueous mixed solution containing a Mo starting material, a V starting material and a Sb starting material; and mixing the composition for catalyst production with the aqueous mixed solution to prepare a precursor slurry.

In this context, the solid niobium starting material and the starting materials, other than an optionally contained organic acid, for preparing the precursor slurry are not particularly limited. For example, the following compounds can be used. Examples of the starting material of Mo include molybdenum oxide, ammonium dimolybdate, ammonium heptamolybdate, phosphomolybdic acid, and silicomolybdic acid. Among them, ammonium heptamolybdate can be suitably used. Examples of the starting material of V include vanadium pentoxide, ammonium metavanadate, and vanadyl sulfate. Among them, ammonium metavanadate can be suitably used. Antimony oxide can be suitably used as the starting material of Sb.

Hereinafter, the preparation of a precursor slurry containing Mo, V, Nb, and Sb will be taken as an example and specifically described. First, ammonium heptamolybdate, ammonium metavanadate, and diantimony trioxide powders are added to water, and the mixture is heated to 80° C. or higher to prepare an aqueous mixed solution. When the catalyst contains a Ce, a compound containing Ce can be mixed at the same time with this operation. For example, cerium nitrate hexahydrate is suitably used as the compound containing Ce.

Next, the composition for catalyst production of the present embodiment prepared earlier is mixed with the aqueous mixed solution according to intended composition to obtain a precursor slurry. When the catalyst contains, for example, W or Ce, a compound containing W or a compound containing Ce is suitably mixed therewith to obtain a precursor slurry.

For example, ammonium metatungstate is suitably used as the compound containing W. For example, cerium nitrate hexahydrate is suitably used as the compound containing Ce. The compound containing W or Ce may be added into the aqueous mixed solution or may be added at the same time with the mixing of the composition for catalyst production with the aqueous mixed solution.

When the catalyst is a catalyst of a composite metal oxide supported on a silica support, the precursor slurry can be prepared so as to contain a silica starting material. In this case, the silica starting material can be appropriately added. For example, a silica sol is suitably used as the silica starting material.

In the case of using antimony, it is preferred to add hydrogen peroxide to the aqueous mixed solution or to a solution containing the components of the aqueous mixed solution in the middle of preparation. In this respect, the molar ratio ($H_2O_2$/Sb) is preferably 0.01 or more and 5 or less, more preferably 0.05 or more and 4 or less. In this respect, it is preferred to continue stirring at 30° C. or higher and 70° C. or lower for 30 minutes or longer and 2 hours or shorter. The precursor slurry obtained in this way may be a homogeneous mixed solution and is usually a slurry.

Drying Step

In the drying step, the precursor slurry obtained by the steps mentioned above is dried to obtain dried particles. The drying can be performed by a method known in the art and can be performed by, for example, spray drying or evaporation to dryness. It is preferred to obtain microspheric dried particles by spray drying. Spraying in the spray drying method can be performed by a centrifugation scheme, a two-fluid nozzle scheme, or a high-pressure nozzle scheme. Steam or air heated with an electric heater or the like can be used as a dry heat source. The temperature of a dryer entrance of a spray drying apparatus is preferably 150° C. or higher and 300° C. or lower, and the temperature of a dryer exit is preferably 100° C. or higher and 160° C. or lower.

Calcination Step

In the calcination step, the dried particles obtained in the drying step are calcined to obtain calcined particles. A rotary kiln can be used as a calcination apparatus. The shape of a calcinator is not particularly limited, and the form of a tube is preferred because continuous calcination can be carried out. The shape of the calcination tube is not particularly limited and is preferably cylindrical. The heating scheme is preferably an external heating system, and an electric furnace can be suitably used.

The size, material, etc. of the calcination tube can be appropriately selected according to calcination conditions or the amount of a product. Its inner diameter is preferably 70 mm or larger and 2000 mm or smaller, more preferably 100 mm or larger and 1200 mm or smaller, and its length is preferably 200 mm or larger and 10000 mm or smaller, more preferably 800 mm or larger and 8000 mm or smaller. In the case of applying impact to a calcinator, the thickness of the calcinator is preferably 2 mm or larger, more preferably 4 mm or larger, from the viewpoint that the calcinator has a sufficient thickness that prevents break ascribable to the impact, and is preferably 100 mm or smaller, more preferably 50 mm or smaller, from the viewpoint that the impact is sufficiently transmitted to the inside of the calcinator. The material of the calcinator is not particularly limited as long as the material has heat resistance and has strength that prevents break ascribable to the impact. SUS can be suitably used.

A weir plate having, in a central part, a hole through which particles pass may be disposed vertically to the flow of the particles in the calcination tube and can thereby partition the calcination tube into two or more zones. The weir plate thus established easily secures a residence time in the calcination tube. The number of weir plates may be one or more. The material of the weir plate is preferably a metal, and the same material as that of the calcination tube can be suitably used. The height of the weir plate can be adjusted according to the residence time to be secured. In the case of supplying particles at 250 g/hr using, for example, a rotary kiln having a SUS calcination tube having an inner diameter of 150 mm and a length of 1150 mm, the height of the weir plate is preferably 5 mm or larger and 50 mm or smaller, more preferably 10 mm or larger and 40 mm or smaller, further preferably 13 mm or larger and 35 mm or smaller. The thickness of the weir plate is not particularly limited and is preferably adjusted according to the size of the calcination tube. In the case of, for example, a rotary kiln having a SUS calcination tube having an inner diameter of 150 mm and a length of 1150 mm, the thickness of the calcination tube is preferably 0.3 mm or larger and 30 mm or smaller, more preferably 0.5 mm or larger and 15 mm or smaller.

The calcination tube is preferably rotated in order to prevent cracks, crazes, etc. in the dried particles and to uniformly calcine the dried particles. The rotation speed of the calcination tube is preferably 0.1 rpm or more and 30 rpm or less, more preferably 0.5 rpm or more and 20 rpm or less, further preferably 1 rpm or more and 10 rpm or less.

For the calcination of the dried particles, it is preferred that the heating temperature of the dried particles should start at a temperature lower than 400° C. and be continuously or intermittently increased to a temperature within the range of 550° C. or higher and 800° C. or lower.

The calcination atmosphere may be an air atmosphere or current of air. At least a portion of the calcination is preferably carried out under current of an inert gas substantially free of oxygen, such as nitrogen. The amount of the inert gas supplied is 50 NL or more, preferably 50 NL or more and 5000 NL or less, more preferably 50 NL or more and 3000 NL or less, per kg of the dried particles (NL means liter (L) measured under normal temperature and pressure conditions, i.e., at 0° C. and 1 atm). In this respect, the flows of the inert gas and the dried particles may be a counter flow or a parallel flow. Counter flow contact is preferred in consideration of gas components generated from the dried particles and a trace amount of air entering together with the dried particles.

The calcination step may be carried out in a single stage. It is preferred that the calcination should consist of preliminary calcination and main calcination; the preliminary calcination should be performed in the temperature range of 250° C. or higher and 400° C. or lower; and the main calcination should be performed in the temperature range of 550° C. or higher and 800° C. or lower. The preliminary calcination and the main calcination may be continuously carried out, or the main calcination may be carried out anew once the preliminary calcination has been completed. The preliminary calcination and the main calcination may each be divided into several stages.

The preliminary calcination is preferably performed at a heating temperature in the range of 250° C. or higher and 400° C. or lower, preferably 300° C. or higher and 400° C. or lower, under current of an inert gas. The temperature is preferably kept constant within the range of 250° C. or higher and 400° C. or lower and may vary or be gradually increased or decreased within the range of 250° C. or higher and 400° C. or lower. The time for which the heating temperature is kept is preferably 30 minutes or longer, more preferably 3 hours or longer and 12 hours or shorter.

A temperature increase pattern until the preliminary calcination temperature is attained may be linear, or the temperature may be increased such that an arc of an upward or downward convex is formed.

An average temperature increase speed during temperature increase until the preliminary calcination temperature is attained is not particularly limited and is usually on the order of 0.1° C./min or more and 15° C./min or less, preferably 0.5° C./min or more and 5° C./min or less, more preferably 1° C./min or more and 2° C./min or less.

The main calcination is preferably carried out at a heating temperature in the range of 550° C. or higher and 800° C. or lower, preferably 580° C. or higher and 750° C. or lower, more preferably 600° C. or higher and 720° C. or lower, further preferably 620° C. or higher and 700° C. or lower, under current of an inert gas. The temperature is preferably kept constant within the range of 620° C. or higher and 700° C. or lower and may vary or be gradually increased or decreased within the range of 620° C. or higher and 700° C. or lower. The main calcination time is 0.5 hours or longer and 20 hours or shorter, preferably 1 hour or longer and 15 hours or shorter.

In the case of partitioning the calcination tube with a weir plate, the dried particles and/or a composite oxide catalyst continuously passes through at least two, preferably 2 or more and 20 or less, more preferably 4 or more and 15 or less zones. The temperature can be controlled using one or more controllers. In order to obtain the desired calcination pattern, a heater and a controller are preferably established in each of the zones partitioned with these weirs, for control. In the case of using, for example, a calcination tube partitioned into eight zones by establishing seven weir plates such that the length of the portion, of the calcination tube, that enters a heating furnace is equally divided into eight, the set temperature of each of the eight zones is preferably controlled with the heater and the controller established in each of the zones such that the temperature of the dried particles and/or the composite oxide catalyst has the desired calcination temperature pattern. The calcination atmosphere under current of an inert gas may be supplemented, if desired, with an oxidizing component (e.g., oxygen) or a reducing component (e.g., ammonia).

A temperature increase pattern until the main calcination temperature is attained may be linear, or the temperature may be increased such that an arc of an upward or downward convex is formed.

An average temperature increase speed during temperature increase until the main calcination temperature is attained is not particularly limited and is generally 0.1° C./min or more and 15° C./min or less, preferably 0.5° C./min or more and 10° C./min or less, more preferably 1° C./min or more and 8° C./min or less.

An average temperature decrease speed after the completion of main calcination is preferably 0.05° C./min or more and 100° C./min or less, more preferably 0.1° C./min or more and 50° C./min or less. It is also preferred to temporarily keep a temperature lower than the main calcination temperature. The temperature to be kept is a temperature lower by 10° C., preferably 50° C., more preferably 100° C., than the main calcination temperature. The time for which the temperature is kept is 0.5 hours or longer, preferably 1 hour or longer, more preferably 3 hours or longer, further preferably 10 hours or longer.

In the case of carrying out main calcination anew once preliminary calcination has been completed, the main calcination is preferably performed by low-temperature treatment.

The time required for the low-temperature treatment, i.e., the time required for decreasing the temperature of the dried particles and/or the composite oxide catalyst and then increasing the temperature to the calcination temperature, can be appropriately adjusted by the size, thickness, or material of the calcinator, the amount of the catalyst produced, a series of periods for continuously calcining the dried particles and/or the composite oxide catalyst, a fixation rate, the amount of fixation, etc. In the case of using, for example, a SUS calcination tube having an inner diameter of 500 mm, a length of 4500 mm, and a thickness of 20 mm, the time is preferably within 30 days, more preferably within 15 days, further preferably within 3 days, particularly preferably within 2 days, during a series of periods for continuously calcining a catalyst.

For example, in the case of supplying the dried particles at a rate of 35 kg/hr while rotating a rotary kiln having a SUS calcination tube having an inner diameter of 500 mm, a length of 4500 mm, and a thickness of 20 mm at 6 rpm, and setting the main calcining temperature to 645° C., a step of lowering the temperature to 400° C. and increasing the temperature to 645° C. can be performed in approximately 1 day. For continuous calcination for 1 year, the calcination can be performed by carrying out such low-temperature treatment at a frequency of once a month while stably maintaining the temperature of an oxide layer.

Catalyst

A catalyst obtained by the method for producing a catalyst according to the present embodiment is, for example, a catalyst containing composite metal oxide represented by the formula (1):

$$Mo_1V_aNb_bSb_cY_dO_n \qquad (1)$$

wherein Y represents at least one or more elements selected from Mn, W, B, Ti, Al, Te, an alkali metal, an alkaline earth metal and a rare earth metal; a, b, c, and d represent atomic ratios of V, Nb, Sb and Y, respectively, per molybdenum (Mo) atom with $0.1 \leq a \leq 1$, $0.01 \leq b \leq 1$, $0.01 \leq c \leq 1$, and $0 \leq d \leq 1$; and n represents the number of oxygen atoms determined by the valence of a constituent element other than oxygen.

The atomic ratios a, b, c, and d per Mo atom are preferably $0.1 \leq a \leq 1$, $0.01 \leq b \leq 1$, $0.01 \leq c \leq 1$, and $0 \leq d \leq 1$, more preferably $0.1 \leq a \leq 0.5$, $0.01 \leq b \leq 0.5$, $0.1 \leq c \leq 0.5$, and $0.0001 \leq d \leq 0.5$, further preferably $0.15 \leq a \leq 0.3$, $0.05 \leq b \leq 0.2$, $0.15 \leq c \leq 0.3$, and $0.0002 \leq d \leq 0.2$, respectively.

In the case of using the catalyst in a fluidized bed, the catalyst is preferably a catalyst of a composite metal oxide supported on a silica support because sufficient strength is required. In the present embodiment, the mass of the silica support is preferably 10% by mass or more and 80% by mass or less, more preferably 20% by mass or more and 60% by mass or less, further preferably 30% by mass or more and 55% by mass or less, in terms of $SiO_2$ based on the total mass of the composite metal oxide and the silica support. The mass of silica serving as a support is preferably 10% by mass or more based on the total mass of the composite metal oxide and the silica from the viewpoint of strength, the prevention of powdering, the ease of safe operation in using the catalyst and reduction in the lost catalyst to be replenished, and is preferably 80% by mass or less based on the total mass of the composite metal oxide and the silica from the viewpoint of achieving sufficient catalytic activity. Particularly, in the case of using the catalyst in a fluidized bed, silica in the amount of 80% by mass or less attains proper specific gravity of the silica-supported catalyst (composite metal oxide+silica support) and easily provides a favorable flow state.

Method for Producing acrylonitrile

One embodiment of the present invention provides a method for producing acrylonitrile. This production method employs a catalyst obtained by the method for producing a catalyst according to the present embodiment. The method for producing acrylonitrile according to the present embodiment is preferably a method for producing acrylonitrile, comprising preparing a catalyst by the method mentioned above, and contacting propane, ammonia and oxygen (molecular oxygen) with the obtained catalyst in a gas phase (gas phase catalytic ammoxidation reaction).

The starting materials for supplying propane and ammonia are not necessarily required to be highly pure, and industrial-grade gases can be used. Air, pure oxygen or air enriched with pure oxygen can be used as a supply oxygen source. Further, helium, neon, argon, carbon dioxide, water vapor, nitrogen or the like may be supplied as a diluting gas.

For ammoxidation reaction, the molar ratio of ammonia to propane to be supplied to the reaction system is 0.3 or more and 1.5 or less, preferably 0.8 or more and 1.2 or less. For both oxidation reaction and ammoxidation reaction, the molar ratio of molecular oxygen to propane to be supplied to the reaction system is 0.1 or more and 6 or less, preferably 0.1 or more and 4 or less.

For both oxidation reaction and ammoxidation reaction, the reaction pressure is 0.5 atm or higher and 5 atm or lower, preferably 1 atm or higher and 3 atm or lower, the reaction temperature is 350° C. or higher and 500° C. or lower, preferably 380° C. or higher and 470° C. or lower, and the contact time is 0.1 sec·g/cc or longer and 10 sec·g/cc or shorter, preferably 0.5 sec·g/cc or longer and 5 sec·g/cc or shorter.

In the present embodiment, the contact time is defined according to the following expression:

$$\text{Contact time (sec·g/cc)}=(W/F)\times 273/(273+T)\times P,$$

wherein

W=the mass (g) of the catalyst,

F=the flow rate (Ncc/sec) of a mixed gas of the starting materials under normal conditions (0° C., 1 atm), T=reaction temperature (° C.), and P=reaction pressure (atm).

The propane conversion rate and the yield of acrylonitrile respectively abide by the following definitions.

Propane conversion rate (%)=(The number of moles of reacted propane)/(The number of moles of supplied propane)×100

Yield of acrylonitrile (%)=(The number of moles of produced acrylonitrile)/(The number of moles of supplied propane)×100

The reaction scheme can adopt a conventional scheme such as a fixed bed, a fluidized bed, or a moving bed. Fluidized bed reaction is preferred, for example, because the removal of reaction heat is easy and can keep the temperature of a catalyst layer almost uniform; the catalyst can be extracted from a reactor during operation; and the catalyst can be further added.

EXAMPLES

Hereinafter, the present embodiment will be described more specifically with reference to Examples. However, the present embodiment is not limited by these Examples by any means.

Example 1

Preparation of Composition for Catalyst Production 137.49 kg of water was added into a mixing vessel and then heated to 50° C. Next, 1.14 kg of oxalic acid dihydrate [$H_2C_2O_4·2H_2O$] was injected thereto and dissolved with stirring. Further, 5.74 kg of hydrogen peroxide water (35.5% by mass in aqueous solution) was injected thereto, followed by the addition of 5.3 kg of niobic acid (75.0% by mass in terms of $Nb_2O_5$). This solution was heated and stirred at 50° C. for 6 hours to obtain a homogeneous mixed solution. The water-soluble mixed solution thereby obtained was used as the composition for catalyst production according to Example 1.

(Nb Concentration, Oxalic Acid Concentration, and Hydrogen Peroxide Concentration of Composition for Catalyst Production)

First, 10 g of the composition for catalyst production was precisely weighed into a crucible, dried at 120° C. for 2 hours, and then heat-treated at 600° C. for 2 hours. The Nb concentration of the composition for catalyst production was calculated from the weight of $Nb_2O_5$ in the obtained solid as described below. [Weight of the solid obtained after calcination (unit: g)]/(265.8/2)/[Weight of the precisely weighed composition for catalyst production (unit: kg)]=[Nb concentration of the composition for catalyst production (unit: mol/kg)]

265.8 is the molecular weight of $Nb_2O_5$ (unit: g/mol).

Also, 3 g of the composition for catalyst production was precisely weighed into a 300 mL glass beaker, and 20 mL of hot water of approximately 80° C. was added thereto, followed by the addition of 10 mL of 1:1 sulfuric acid. The mixed solution obtained in this way was titrated using ¼ N $KMnO_4$ with stirring while the solution temperature was kept at 70° C. in a water bath. A point at which faint light pink color ascribable to $KMnO_4$ lasted for approximately 30 seconds or longer was defined as an end-point. The total concentration of oxalic acid and hydrogen peroxide was calculated from the titer according to the following expressions.

$$2KMnO_4+3H_2SO_4+5H_2C_2O_4\rightarrow K_2SO_4+2MnSO_4+10CO_2+8H_2O$$

$$2KMnO_4+3H_2SO_4+5H_2O_2\rightarrow K_2SO_4+2MnSO_4+5O_2+8H_2O$$

If precipitation was found in the composition for catalyst production in the measurement described above, the supernatant was separated from the precipitates by decantation and the concentration of the supernatant portion was measured.

The oxalic acid concentration was quantified by ion chromatography.

The ion chromatography analysis was conducted using an ion chromatography system IC-2010 from Tosoh Corp. and a column TSKgel SuperIC-AZ (4.6 mm I.D.×15 cm) in the suppressor mode. 30 μL of a sample diluted 500-fold was injected to the column, and the concentration was analyzed by the absolute calibration curve method.

The concentration of hydrogen peroxide was calculated from the difference between the total concentration of oxalic acid and hydrogen peroxide determined by titration and the oxalic acid concentration determined by ion chromatography.

The Nb concentration, the hydrogen peroxide concentration, and the oxalic acid concentration of the obtained composition for catalyst production were measured by the procedures described above, and molar ratios (oxalic acid/Nb; indicated by "Ox/Nb" in the tables, hydrogen peroxide/Nb; indicated by "$H_2O_2$/Nb" in the tables) were calculated.

The concentration of each component was also measured in the same manner as in Example 1 as to the compositions for catalyst production according to Examples 2 to 5 and Comparative Examples 1 to 3 prepared as mentioned later.

Example 2

A homogeneous mixed solution was obtained in the same manner as in Example 1 except that the amount of water was set to 57.95 kg; the amount of hydrogen peroxide water added was set to 86.03 kg; and the amount of oxalic acid dihydrate [$H_2C_2O_4·2H_2O$] added was set to 0.38 kg. The water-soluble mixed solution thereby obtained was used as the composition for catalyst production according to Example 2.

Example 3

A homogeneous mixed solution was obtained in the same manner as in Example 1 except that the amount of water was set to 15.32 kg; the amount of hydrogen peroxide water added was set to 129.05 kg; and no oxalic acid dihydrate was added. The water-soluble mixed solution thereby obtained was used as the composition for catalyst production according to Example 3.

Example 4

A homogeneous mixed solution was obtained in the same manner as in Example 1 except that the amount of niobic acid added was set to 12.20 kg; the amount of oxalic acid dihydrate [$H_2C_2O_4 \cdot 2H_2O$] added was set to 13.09 kg; the amount of water was set to 98.00 kg; and the amount of hydrogen peroxide water added was set to 26.38 kg. The water-soluble mixed solution thereby obtained was used as the composition for catalyst production according to Example 4.

Example 5

A homogeneous mixed solution was obtained in the same manner as in Example 1 except that the amount of niobic acid added was set to 12.20 kg; the amount of oxalic acid dihydrate [$H_2C_2O_4 \cdot 2H_2O$] added was set to 13.09 kg; the amount of water was set to 111.19 kg; and the amount of hydrogen peroxide water added was set to 13.19 kg. The water-soluble mixed solution thereby obtained was used as the composition for catalyst production according to Example 5.

Example 6

A homogeneous mixed solution was obtained in the same manner as in Example 1 except that the amount of niobic acid added was set to 12.20 kg; the amount of oxalic acid dihydrate [$H_2C_2O_4 \cdot 2H_2O$] added was set to 0.87 kg; the amount of water was set to 4.68 kg; and the amount of hydrogen peroxide water added was set to 131.92 kg. The water-soluble mixed solution thereby obtained was used as the composition for catalyst production according to Example 6.

Example 7

A homogeneous mixed solution was obtained in the same manner as in Example 1 except that the amount of niobic acid added was set to 17.24 kg; the amount of oxalic acid dihydrate [$H_2C_2O_4 \cdot 2H_2O$] added was set to 12.33 kg; the amount of water was set to 82.82 kg; and the amount of hydrogen peroxide water added was set to 37.28 kg. The water-soluble mixed solution thereby obtained was used as the composition for catalyst production according to Example 7.

Example 8

A homogeneous mixed solution was obtained in the same manner as in Example 1 except that the amount of niobic acid added was set to 18.61 kg; the amount of water was set to 10.68 kg; the amount of hydrogen peroxide water added was set to 120.71 kg; and no oxalic acid dihydrate was added. The water-soluble mixed solution thereby obtained was used as the composition for catalyst production according to Example 8.

Example 9

A homogeneous mixed solution was obtained in the same manner as in Example 1 except that the amount of niobic acid added was set to 18.61 kg; the amount of oxalic acid dihydrate [$H_2C_2O_4 \cdot 2H_2O$] added was set to 6.65 kg; the amount of water was set to 24.15 kg; and the amount of hydrogen peroxide water added was set to 100.59 kg. The water-soluble mixed solution thereby obtained was used as the composition for catalyst production according to Example 9.

Example 10

A homogeneous mixed solution was obtained in the same manner as in Example 1 except that the amount of niobic acid added was set to 18.61 kg; the amount of oxalic acid dihydrate [$H_2C_2O_4 \cdot 2H_2O$] added was set to 19.96 kg; the amount of water was set to 101.38 kg; and the amount of hydrogen peroxide water added was set to 10.06 kg. The water-soluble mixed solution thereby obtained was used as the composition for catalyst production according to Example 10.

Example 11

A homogeneous mixed solution was obtained in the same manner as in Example 1 except that the amount of niobic acid added was set to 18.61 kg; the amount of oxalic acid dihydrate [$H_2C_2O_4 \cdot 2H_2O$] added was set to 21.29 kg; the amount of water was set to 9.51 kg; and the amount of hydrogen peroxide water added was set to 100.59 kg. The water-soluble mixed solution thereby obtained was used as the composition for catalyst production according to Example 11.

Example 12

A homogeneous mixed solution was obtained in the same manner as in Example 1 except that the amount of niobic acid added was set to 18.61 kg; the amount of oxalic acid dihydrate [$H_2C_2O_4 \cdot 2H_2O$] added was set to 22.62 kg; the amount of water was set to 98.72 kg; and the amount of hydrogen peroxide water added was set to 10.06 kg. The water-soluble mixed solution thereby obtained was used as the composition for catalyst production according to Example 12.

Example 13

A homogeneous mixed solution was obtained in the same manner as in Example 1 except that the amount of niobic acid added was set to 18.61 kg; the amount of oxalic acid dihydrate [$H_2C_2O_4 \cdot 2H_2O$] added was set to 23.95 kg; the amount of water was set to 97.39 kg; and the amount of hydrogen peroxide water added was set to 10.06 kg. The water-soluble mixed solution thereby obtained was used as the composition for catalyst production according to Example 13.

Example 14

A homogeneous mixed solution was obtained in the same manner as in Example 1 except that the amount of niobic acid added was set to 18.57 kg; the amount of oxalic acid dihydrate [$H_2C_2O_4 \cdot 2H_2O$] added was set to 26.55 kg; the amount of water was set to 99.56 kg; and the amount of hydrogen peroxide water added was set to 5.02 kg. The water-soluble mixed solution thereby obtained was used as the composition for catalyst production according to Example 14.

Comparative Example 1

Preparation of Composition for Catalyst Production 83.12 kg of water was added into a mixing vessel and then heated to 40° C. Next, 52.27 kg of oxalic acid dihydrate [$H_2C_2O_4 \cdot 2H_2O$] was injected thereto with stirring, followed by the injection of 14.62 kg of niobic acid containing 75.0% by mass of $Nb_2O_5$. Both of the materials were mixed in water. This solution was heated and stirred at 95° C. for 4 hours. The aqueous mixed solution thereby obtained was allowed to cool naturally with stirring and thereby cooled to 40° C. Then, the mixed solution was cooled to 2° C. at −10° C./hr and left for 1 hour. Subsequently, a mixture of a deposited solid and the mixed solution was injected to a filter, and the deposited solid was filtered off to obtain a homogeneous mixed solution. The water-soluble mixed solution thereby obtained was used as the composition for catalyst production according to Comparative Example 1.

Comparative Example 2

Preparation of Composition for Catalyst Production 75.14 kg of water was added into a mixing vessel and then heated to 50° C. Next, 57.4 kg of oxalic acid dihydrate [$H_2C_2O_4 \cdot 2H_2O$] was injected thereto with stirring, followed by the injection of 17.49 kg of niobic acid containing 76.3% by mass of $Nb_2O_5$. Both of the materials were mixed in water. This solution was heated and stirred at 90° C. for 6 hours. The aqueous mixed solution thereby obtained was allowed to cool naturally with stirring and thereby cooled to 40° C. Then, the mixed solution was cooled to 2° C. at −10° C./hr and left for 1 hour. Subsequently, a mixture of a deposited solid and the mixed solution was injected to a filter, and the deposited solid was filtered off to obtain a homogeneous mixed solution. The water-soluble mixed solution thereby obtained was used as the composition for catalyst production according to Comparative Example 2.

Comparative Example 3

Preparation of Composition for Catalyst Production 76.38 kg of water was added into a mixing vessel and then heated to 50° C. Next, 54.74 kg of oxalic acid dihydrate [$H_2C_2O_4 \cdot 2H_2O$] was injected thereto with stirring, followed by the injection of 18.89 kg of niobic acid containing 76.0% by mass of $Nb_2O_5$. Both of the materials were mixed in water. This solution was heated and stirred at 95° C. for 3 hours. The aqueous mixed solution thereby obtained was allowed to cool naturally with stirring and thereby cooled to 40° C. Then, the mixed solution was cooled to 2° C. at −10° C./hr and left for 1 hour. Subsequently, a mixture of a deposited solid and the mixed solution was injected to a filter, and the deposited solid was filtered off to obtain a homogeneous mixed solution. The water-soluble mixed solution thereby obtained was used as the composition for catalyst production according to Comparative Example 3.

Comparative Example 4

Preparation of Composition for Catalyst Production 4.08 kg of water and 79.04 g of hydrogen peroxide water (35.5% by mass in aqueous solution) were added into a mixing vessel and then heated to 40° C. Next, 52.3 kg of oxalic acid dihydrate [$H_2C_2O_4 \cdot 2H_2O$] was injected thereto with stirring, followed by the injection of 14.62 kg of niobic acid containing 75.0% by mass of $Nb_2O_5$. Both of the materials were mixed in water. This solution was heated and stirred at 95° C. for 4 hours. The aqueous mixed solution thereby obtained was allowed to cool naturally with stirring and thereby cooled to 40° C. Then, the mixed solution was cooled to 2° C. at −10° C./hr and left for 1 hour. Subsequently, a mixture of a deposited solid and the mixed solution was injected to a filter, and the deposited solid was filtered off to obtain a homogeneous mixed solution. The water-soluble mixed solution thereby obtained was used as the composition for catalyst production according to Comparative Example 4.

Production of Catalyst

Catalyst Production Example 1

A catalyst was produced using the composition for catalyst production according to Example 1 as follows such that the composition of composite metal oxide was $Mo_1V_{0.24}Nb_{0.15}Sb_{0.27}W_{0.03}Ce_{0.005}O_n$ (n is determined depending on the valence of a constituent element other than oxygen).

Preparation of Precursor Slurry

To 24.27 kg of water, 4.03 kg of ammonium heptamolybdate [$(NH_4)6Mo_7O_{24} \cdot 4H_2O$], 0.64 kg of ammonium metavanadate [$NH_4VO_3$], 0.89 kg of diantimony trioxide [$Sb_2O_3$], and 0.05 kg of cerium nitrate were added, and the mixture was heated at 95° C. for 1 hour with stirring to prepare an aqueous mixed solution (B1).

The obtained aqueous mixed solution (B1) was cooled to 70° C. Then, to the resulting aqueous mixed solution (B1), 7.04 kg of a silica sol containing 34.0% by mass of $SiO_2$ was added, further 1.78 kg of hydrogen peroxide water containing 35.5% by mass of $H_2O_2$ was added, and stirring was continued at 55° C. for 30 minutes. To the resulting solution, 17.01 kg of the composition for catalyst production obtained in Example 1 (containing 0.45 kg of niobium oxide as a weight in terms of niobium oxide ($Nb_2O_5$)), a dispersion containing 2.4 kg of powder silica (manufactured by Nippon Aerosil Co., Ltd., trade name "Aerosil 200") dispersed in 21.6 kg of water, and 0.319 kg of an ammonium metatungstate solution containing 50.2% by weight of tungsten oxide were further added in order, followed by stirring at 50° C. for 2.5 hours to obtain a precursor slurry (D1).

Preparation of Dried Particles (E1)

Next, the precursor slurry (D1) obtained as mentioned above was supplied to a centrifugal spray dryer and dried to obtain microspheric dried particles (E1) having an average particle size of 51 μm. The temperature of the entrance of the dryer was 210° C., and the temperature of the exit was 120° C.

Calcination of Dried Particles (E1)

A SUS calcination tube having an inner diameter of 3 inches (76 mm), a length of 300 mm, and a thickness of 3 mm was charged with 500 g of the dried particles (E1) obtained as mentioned above. While the calcination tube was rotated around an axis in the length direction under current of 5.0 NL/min nitrogen gas, preliminary calcination and main calcination were performed. In the preliminary calcination, the temperature was increased at a temperature increase speed of 0.75° C./min to 340° C. from room temperature, and the calcination was performed at 340° C. for 1 hour. Subsequently, in the main calcination, the temperature was increased at a temperature increase speed of 3° C./min to 670° C. from 340° C., kept at 670° C. for 2 hours, and then decreased at a temperature decrease speed of 1° C./min to 350° C. for calcination to obtain a calcined form (F1).

Removal of Protrusion

Protrusions present on the surface of the catalyst particles were removed by the method described below. 50 g of the calcined form (F1) was injected to a vertical tube (inner diameter: 41.6 mm, length: 70 cm) equipped with a perforated disc having three holes of 1/64 inches in diameter at the bottom and provided with a paper filter at the upper part. In this respect, the length of air stream in the direction of air stream flowing was 52 mm, and the average linear velocity of the air stream was 310 m/s. A composite oxide catalyst (G1) obtained 24 hours later had no protrusion.

Catalyst Production Examples 2 and 3

The catalysts according to Catalyst Production Examples 2 and 3 were produced in the same manner as in Catalyst Production Example 1 except that 17.01 kg each of the compositions for catalyst production according to Examples 2 and 3, respectively, was used instead of 17.01 kg of the composition for catalyst production according to Example 1.

Catalyst Production Examples 4 to 6

The catalysts according to Catalyst Production Examples 4 to 6 were produced in the same manner as in Catalyst Production Example 1 except that 7.40 kg each of the compositions for catalyst production according to Examples 4 to 6, respectively, which corresponded to 0.45 kg as the weight of niobium oxide was used instead of 17.01 kg of the composition for catalyst production according to Example 1, which corresponded to 0.45 kg as the weight of niobium oxide.

Catalyst Production Example 7

The catalyst according to Catalyst Production Example 7 was produced in the same manner as in Catalyst Production Example 1 except that 5.24 kg of the composition for catalyst production according to Example 7, which corresponded to 0.45 kg as the weight of niobium oxide was used instead of 17.01 kg of the composition for catalyst production according to Example 1, which corresponded to 0.45 kg as the weight of niobium oxide.

Catalyst Production Examples 8 to 14

The catalysts according to Catalyst Production Examples 8 to 14 were produced in the same manner as in Catalyst Production Example 1 except that 4.86 kg each of the compositions for catalyst production according to Examples 8 to 14, respectively, which corresponded to 0.45 kg as the weight of niobium oxide was used instead of 17.01 kg of the composition for catalyst production according to Example 1, which corresponded to 0.45 kg as the weight of niobium oxide.

Comparative Catalyst Production Example 1

The catalyst according to Comparative Catalyst Production Example 1 was produced in the same manner as in Catalyst Production Example 1 except that 4.54 kg of the composition for catalyst production according to Comparative Example 1, which corresponded to 0.45 kg as the weight of niobium oxide was used instead of 17.01 kg of the composition for catalyst production according to Example 1, which corresponded to 0.45 kg as the weight of niobium oxide.

Comparative Catalyst Production Example 2

The catalyst according to Comparative Catalyst Production Example 2 was produced in the same manner as in Catalyst Production Example 1 except that 3.78 kg of the composition for catalyst production according to Comparative Example 2, which corresponded to 0.45 kg as the weight of niobium oxide was used instead of 17.01 kg of the composition for catalyst production according to Example 1, which corresponded to 0.45 kg as the weight of niobium oxide.

Comparative Catalyst Production Example 3

The catalyst according to Comparative Catalyst Production Example 3 was produced in the same manner as in Catalyst Production Example 1 except that 4.73 kg of the composition for catalyst production according to Comparative Example 3, which corresponded to 0.45 kg as the weight of niobium oxide was used instead of 17.01 kg of the composition for catalyst production according to Example 1, which corresponded to 0.45 kg as the weight of niobium oxide.

Comparative Catalyst Production Example 4

The catalyst according to Comparative Catalyst Production Example 4 was produced in the same manner as in Catalyst Production Example 1 except that 4.48 kg of the composition for catalyst production according to Comparative Example 4, which corresponded to 0.45 kg as the weight of niobium oxide was used instead of 17.01 kg of the composition for catalyst production according to Example 1, which corresponded to 0.45 kg as the weight of niobium oxide.

Catalyst Production Example 15

The catalyst according to Catalyst Production Example 15 was produced such that the composition of composite metal oxide was $Mo_1V_{0.17}Nb_{0.14}Sb_{0.27}W_{0.003}Ce_{0.005}O_n$ (n is determined depending on the valence of a constituent element other than oxygen) in the same manner as in Catalyst Production Example 10 except that the preparation of the precursor slurry in Catalyst Production Example 10 was changed as follows.

Preparation of Precursor Slurry

To 22.13 kg of water, 4.17 kg of ammonium heptamolybdate $[(NH_4)6Mo_7O_{24}\cdot 4H_2O]$, 0.47 kg of ammonium metavanadate $[NH_4VO_3]$, 0.93 kg of diantimony trioxide $[Sb_2O_3]$, and 0.05 kg of cerium nitrate were added, and the mixture was heated at 95° C. for 1 hour with stirring to prepare an aqueous mixed solution (B1).

The obtained aqueous mixed solution (B1) was cooled to 70° C. Then, to the resulting aqueous mixed solution (B1), 7.04 kg of a silica sol containing 34.0% by mass of $SiO_2$ was added, further 1.78 kg of hydrogen peroxide water containing 35.5% by mass of $H_2O_2$ was added, and stirring was continued at 55° C. for 30 minutes. To the resulting solution, 4.70 kg of the composition for catalyst production obtained in Example 10 (containing 0.44 kg of niobium oxide as a weight in terms of niobium oxide ($Nb_2O_5$)), a dispersion containing 2.4 kg of powder silica (manufactured by Nippon Aerosil Co., Ltd., trade name "Aerosil 200") dispersed in 21.6 kg of water, and 0.325 kg of an ammonium metatungstate solution containing 50.2% by weight of tungsten oxide were further added in order, followed by stirring at 50° C. for 2.5 hours to obtain a precursor slurry (D1).

Comparative Catalyst Production Example 5

The catalyst according to Comparative Catalyst Production Example 5 was produced in the same manner as in Catalyst Production Example 15 except that 4.90 kg of the composition for catalyst production (containing 0.44 kg of niobium oxide as a weight in terms of niobium oxide ($Nb_2O_5$)) obtained in Comparative Example 2 was used instead of the composition for catalyst production according to Example 10.

Catalyst Production Example 16

The catalyst according to Catalyst Production Example 16 was produced such that the composition of composite metal oxide was $Mo_1V_{0.24}Nb_{0.19}Sb_{0.18}W_{0.005}Ce_{0.005}O_n$ (n is determined depending on the valence of a constituent element other than oxygen) in the same manner as in Catalyst Production Example 10 except that the preparation of the precursor slurry in Catalyst Production Example 10 was changed as follows.

Preparation of Precursor Slurry

To 20.91 kg of water, 4.28 kg of ammonium heptamolybdate $[(NH_4)6Mo_7O_{24}\cdot 4H_2O]$, 0.68 kg of ammonium metavanadate $[NH_4VO_3]$, 0.63 kg of diantimony trioxide $[Sb_2O_3]$, and 0.05 kg of cerium nitrate were added, and the mixture was heated at 95° C. for 1 hour with stirring to prepare an aqueous mixed solution (B1).

The obtained aqueous mixed solution (B1) was cooled to 70° C. Then, to the resulting aqueous mixed solution (B1), 7.04 kg of a silica sol containing 34.0% by mass of $SiO_2$ was added, further 1.78 kg of hydrogen peroxide water containing 35.5% by mass of $H_2O_2$ was added, and stirring was continued at 55° C. for 30 minutes. To the resulting solution, 6.54 kg of the composition for catalyst production obtained in Example 10 (containing 0.61 kg of niobium oxide as a weight in terms of niobium oxide ($Nb_2O_5$)), a dispersion containing 2.4 kg of powder silica (manufactured by Nippon Aerosil Co., Ltd., trade name "Aerosil 200") dispersed in 21.6 kg of water, and 0.056 kg of an ammonium metatungstate solution containing 50.2% by weight of tungsten oxide were further added in order, followed by stirring at 50° C. for 2.5 hours to obtain a precursor slurry (D1).

Comparative Catalyst Production Example 6

The catalyst according to Comparative Catalyst Production Example 6 was produced in the same manner as in Catalyst Production Example 16 except that 6.83 kg of the composition for catalyst production (containing 0.61 kg of niobium oxide as a weight in terms of niobium oxide ($Nb_2O_5$)) obtained in Comparative Example 2 was used instead of the composition for catalyst production according to Example 10.

Catalyst Production Example 17

The catalyst according to Catalyst Production Example 17 was produced such that the composition of composite metal oxide was $Mo_1V_{0.25}Nb_{0.1}Sb_{0.27}W_{0.05}Ce_{0.005}O_n$ (n is determined depending on the valence of a constituent element other than oxygen) in the same manner as in Catalyst Production Example 10 except that the preparation of the precursor slurry in Catalyst Production Example 10 was changed as follows.

Preparation of Precursor Slurry

To 23.99 kg of water, 4.05 kg of ammonium heptamolybdate $[(NH_4)6Mo_7O_{24}\cdot 4H_2O]$, 0.67 kg of ammonium metavanadate $[NH_4VO_3]$, 0.90 kg of diantimony trioxide $[Sb_2O_3]$, and 0.05 kg of cerium nitrate were added, and the mixture was heated at 95° C. for 1 hour with stirring to prepare an aqueous mixed solution (B1).

The obtained aqueous mixed solution (B1) was cooled to 70° C. Then, to the resulting aqueous mixed solution (B1), 7.04 kg of a silica sol containing 34.0% by mass of $SiO_2$ was added, further 1.78 kg of hydrogen peroxide water containing 35.5% by mass of $H_2O_2$ was added, and stirring was continued at 55° C. for 30 minutes. To the resulting solution, 3.26 kg of the composition for catalyst production obtained in Example 10 (containing 0.30 kg of niobium oxide as a weight in terms of niobium oxide ($Nb_2O_5$)), a dispersion containing 2.4 kg of powder silica (manufactured by Nippon Aerosil Co., Ltd., trade name "Aerosil 200") dispersed in 21.6 kg of water, and 0.526 kg of an ammonium metatungstate solution containing 50.2% by weight of tungsten oxide were further added in order, followed by stirring at 50° C. for 2.5 hours to obtain a precursor slurry (D1).

Comparative Catalyst Production Example 7

The catalyst according to Comparative Catalyst Production Example 7 was produced in the same manner as in Catalyst Production Example 17 except that 3.40 kg of the composition for catalyst production (containing 0.30 kg of niobium oxide as a weight in terms of niobium oxide ($Nb_2O_5$)) obtained in Comparative Example 2 was used instead of the composition for catalyst production according to Example 10.

Catalyst Production Example 18

The catalyst according to Catalyst Production Example 18 was produced such that the composition of composite metal oxide was $Mo_1V_{0.25}Nb_{0.14}Sb_{0.26}W_{0.05}Ti_{0.05}Mn_{0.03}Ce_{0.01}O_n$ (n is determined depending on the valence of a constituent element other than oxygen) in the same manner as in Catalyst Production Example 10 except that the preparation of the precursor slurry in Catalyst Production Example 10 was changed as follows.

Preparation of Precursor Slurry

To 25.45 kg of water, 3.97 kg of ammonium heptamolybdate $[(NH_4)6Mo_7O_{24}\cdot 4H_2O]$, 0.65 kg of ammonium metavanadate $[NH_4VO_3]$, 0.85 kg of diantimony trioxide $[Sb_2O_3]$, 0.328 kg of ammonium titanyl oxalate monohydrate, 0.192 kg of manganese nitrate hexahydrate and 0.10 kg of cerium nitrate were added, and the mixture was heated at 95° C. for 1 hour with stirring to prepare an aqueous mixed solution (B1).

The obtained aqueous mixed solution (B1) was cooled to 70° C. Then, to the resulting aqueous mixed solution (B1), 7.04 kg of a silica sol containing 34.0% by mass of $SiO_2$ was added, further 1.78 kg of hydrogen peroxide water containing 35.5% by mass of $H_2O_2$ was added, and stirring was continued at 55° C. for 30 minutes. To the resulting solution, 4.47 kg of the composition for catalyst production obtained in Example 1 (containing 0.42 kg of niobium oxide as a weight in terms of niobium oxide ($Nb_2O_5$)), a dispersion containing 2.4 kg of powder silica (manufactured by Nippon Aerosil Co., Ltd., trade name "Aerosil 200") dispersed in 21.6 kg of water, and 0.516 kg of an ammonium metatungstate solution containing 50.2% by weight of tungsten oxide were further added in order, followed by stirring at 50° C. for 2.5 hours to obtain a precursor slurry (D1).

Comparative Catalyst Production Example 8

The catalyst according to Comparative Catalyst Production Example 7 was produced in the same manner as in Catalyst Production Example 18 except that 4.67 kg of the composition for catalyst production (containing 0.42 kg of niobium oxide as a weight in terms of niobium oxide ($Nb_2O_5$)) obtained in Comparative Example 2 was used instead of the composition for catalyst production according to Example 10.

Measurement of Acrylonitrile Yield

Acrylonitrile was produced as follows using the catalyst obtained in each of Catalyst Production Examples and Comparative Catalyst Production Examples. The results are shown in Tables 1 to 2.

A Vycor glass fluidized bed reaction tube having an inner diameter of 25 mm was charged with 35 g of the oxide catalyst. The reaction temperature was set to 440° C., and the reaction pressure was set to ordinary pressure. A mixed gas of propane:ammonia:oxygen:helium at a molar ratio of 1:1:3:18 was supplied thereto for a contact time of 2.8 (sec·g/cc).

TABLE 1

| | | Composition of starting material in composition for catalyst production | | | Composition of finished solution of composition for catalyst production | | | | | | Ratio of discarded oxalic acid to starting material oxalic acid | | Intensity ratio of |
|---|---|---|---|---|---|---|---|---|---|---|---|---|---|
| | Catalyst | Nb concentration (mol/kg) | Ox*[1] concentration (mol/kg) | $H_2O_2$/Nb ratio | Nb concentration (mol/kg) | Ox concentration mol/kg) | Ox/Nb ratio | Ox/Nb ratio (after left standing for 1 day) | $H_2O_2$ concentration (mol/kg) | $H_2O_2$/Nb ratio | (wt %) | Catalyst AN yield (%) | Raman spectrum peaks (Y/X)*[2] |
| Example 1 | Catalyst Production Example 1 | 0.20 | 0.06 | 2.0 | 0.20 | 0.06 | 0.3 | 0.3 | 0.4 | 2.0 | 0 | 57 | 0.2 |
| Example 2 | Catalyst Production Example 2 | 0.20 | 0.02 | 30.0 | 0.20 | 0.02 | 0.1 | 0.1 | 6 | 30.0 | 0 | 57.1 | 0.1 |
| Example 3 | Catalyst Production Example 3 | 0.20 | 0 | 45.0 | 0.20 | 0 | 0.0 | 0.0 | 9 | 45.0 | 0 | 57.0 | 0.0 |
| Example 4 | Catalyst Production Example 4 | 0.46 | 0.69 | 4.0 | 0.46 | 0.69 | 1.5 | 1.5 | 1.84 | 4.0 | 0 | 56.6 | 0.4 |
| Example 5 | Catalyst Production Example 5 | 0.46 | 0.69 | 2.0 | 0.46 | 0.69 | 1.5 | 1.5 | 0.92 | 2.0 | 0 | 56.7 | 0.4 |
| Example 6 | Catalyst Production Example 6 | 0.46 | 0.046 | 20.0 | 0.46 | 0.046 | 0.1 | 0.1 | 9.2 | 20.0 | 0 | 57.1 | 0.0 |
| Example 7 | Catalyst Production Example 7 | 0.65 | 0.65 | 4.0 | 0.65 | 0.65 | 1.0 | 1.0 | 2.60 | 4.0 | 0 | 56.9 | 0.3 |
| Example 8 | Catalyst Production Example 8 | 0.70 | 0 | 12.0 | 0.70 | 0 | 0.0 | 0.0 | 8.40 | 12.0 | 0 | 57.1 | 0.0 |
| Example 9 | Catalyst Production Example 9 | 0.70 | 0.35 | 10.0 | 0.70 | 0.35 | 0.5 | 0.5 | 7.00 | 10.0 | 0 | 56.9 | 0.2 |
| Example 10 | Catalyst Production Example 10 | 0.70 | 1.05 | 1.0 | 0.70 | 1.05 | 1.5 | 1.5 | 0.70 | 1.0 | 0 | 56.6 | 0.4 |
| Example 11 | Catalyst Production Example 11 | 0.70 | 1.12 | 10.0 | 0.70 | 1.12 | 1.6 | 1.6 | 7.00 | 10.0 | 0 | 56.5 | 0.5 |
| Example 12 | Catalyst Production Example 12 | 0.70 | 1.19 | 1.0 | 0.70 | 1.19 | 1.7 | 1.7 | 0.70 | 1.0 | 0 | 56.5 | 0.6 |
| Example 13 | Catalyst Production Example 13 | 0.70 | 1.26 | 1.0 | 0.70 | 1.26 | 1.8 | 1.8 | 0.70 | 1.0 | 0 | 56.4 | 0.7 |
| Example 14 | Catalyst Production Example 14 | 0.70 | 1.40 | 0.5 | 0.70 | 1.40 | 2.0 | 2.0 | 0.35 | 0.5 | 0 | 56.3 | 0.8 |
| Comparative Example 1 | Comparative Catalyst Production Example 1 | 0.55 | 2.75 | 0 | 0.75 | 1.79 | 2.39 | 2.39 | 0 | 0 | 52.2 | 55.6 | 2.1 |

TABLE 1-continued

| | Catalyst | Composition of starting material in composition for catalyst production: Nb concentration (mol/kg) | Ox*[1] concentration (mol/kg) | $H_2O_2$/Nb ratio | Composition of finished solution of composition for catalyst production: Nb concentration (mol/kg) | Ox concentration mol/kg) | Ox/Nb ratio | Ox/Nb ratio (after left standing for 1 day) | $H_2O_2$ concentration (mol/kg) | $H_2O_2$/Nb ratio | Ratio of discarded oxalic acid to starting material oxalic acid (wt %) | Catalyst AN yield (%) | Intensity ratio of Raman spectrum peaks (Y/X)*[2] |
|---|---|---|---|---|---|---|---|---|---|---|---|---|---|
| Comparative Example 2 | Comparative Catalyst Production Example 2 | 0.67 | 3.02 | 0 | 0.90 | 2.01 | 2.23 | 2.23 | 0 | 0 | 50.4 | 55.7 | 1.8 |
| Comparative Example 3 | Comparative Catalyst Production Example 3 | 0.72 | 2.88 | 0 | 0.72 | 1.82 | 2.52 | 2.52 | 0 | 0 | 37 | 55.0 | 2.5 |
| Comparative Example 4 | Comparative Catalyst Production Example 4 | 0.55 | 2.75 | 10 | 0.76 | 1.76 | 2.31 | 2.31 | 7.6 | 10 | 50.5 | 55.7 | 2.0 |

*[1]Ox = oxalic acid

*[2]Ratio of intensity Y of the largest peak observed in the range of 890 cm-1 or more and 1000 cm-1 or less to intensity X of the largest peak observed in the range of 500 cm-1 or more and 650 cm-1 or less (Y/X)

TABLE 2

| | Composition for catalyst production | Composition of starting material in composition for catalyst production: Nb concentration (mol/kg) | Ox*[1] concentration (mol/kg) | $H_2O_2$/Nb ratio | Composition of finished solution of composition for catalyst production: Nb concentration (mol/kg) | Ox concentration (mol/kg) | Ox/Nb ratio | Ox/Nb ratio (after left standing for 1 day) | $H_2O_2$ concentration (mol/kg) | $H_2O_2$/Nb ratio | Ratio of discarded oxalic acid to starting material oxalic acid (wt %) | Catalyst AN yield (%) | Intensity ratio of Raman spectrum peaks (Y/X)*[2] |
|---|---|---|---|---|---|---|---|---|---|---|---|---|---|
| Catalyst Production Example 15 | Example 10 | 0.70 | 1.05 | 1.0 | 0.70 | 1.05 | 1.5 | 1.5 | 0.70 | 1.0 | 0 | 56.7 | 0.4 |
| Comparative Catalyst Production Example 5 | Comparative Example 2 | 0.67 | 3.02 | 0 | 0.90 | 2.01 | 2.23 | 2.23 | 0 | 0 | 50.4 | 55.8 | 1.8 |
| Catalyst Production Example 16 | Example 10 | 0.70 | 1.05 | 1.0 | 0.70 | 1.05 | 1.5 | 1.5 | 0.70 | 1.0 | 0 | 56.5 | 0.4 |
| Comparative Catalyst Production Example 6 | Comparative Example 2 | 0.67 | 3.02 | 0 | 0.90 | 2.01 | 2.23 | 2.23 | 0 | 0 | 50.4 | 55.5 | 1.8 |
| Catalyst Production Example 17 | Example 10 | 0.70 | 1.05 | 1.0 | 0.70 | 1.05 | 1.5 | 1.5 | 0.70 | 1.0 | 0 | 56.6 | 0.4 |
| Comparative Catalyst Production Example 7 | Comparative Example 2 | 0.67 | 3.02 | 0 | 0.90 | 2.01 | 2.23 | 2.23 | 0 | 0 | 50.4 | 55.6 | 1.8 |
| Catalyst Production Example 18 | Example 10 | 0.70 | 1.05 | 1.0 | 0.70 | 1.05 | 1.5 | 1.5 | 0.70 | 1.0 | 0 | 56.4 | 0.4 |
| Comparative Catalyst Production Example 8 | Comparative Example 2 | 0.67 | 3.02 | 0 | 0.90 | 2.01 | 2.23 | 2.23 | 0 | 0 | 50.4 | 55.4 | 1.8 |

*[1]Ox = oxalic acid

*[2] Ratio of intensity Y of the largest peak observed in the range of 890 cm-1 or more and 1000 cm-1 or less to intensity X of the largest peak observed in the range of 500 cm-1 or more and 650 cm-1 or less (Y/X)

Analysis by Raman Spectroscopy

Measurement by Raman spectroscopy was performed using the composition for catalyst production obtained in each example described above. The Raman spectroscopy apparatus used was RENISHAW in Via Qontor. The measurement was performed under conditions involving an excitation laser wavelength of 532 nm, a laser output of 27.1 mW, a light exposure time of 5 sec, and 10 scans. FIG. 1 shows the Raman spectra of Example 4 and Comparative Example 2 obtained by measurement.

Y/X was calculated from intensity X of the largest peak observed in the range of 500 $cm^{-1}$ or more and 650 $cm^{-1}$ or less and intensity Y of the largest peak observed in the range of 890 $cm^{-1}$ or more and 1000 $cm^{-1}$ or less. The presence or absence of a peak in the range of 685 $cm^{-1}$ or more and 785 $cm^{-1}$ or less was confirmed. If a sample emits fluorescence at the excitation laser wavelength described above, accurate measurement is impossible. Therefore, a wavelength at which a sample emits no fluorescence is selected and used from among different excitation laser wavelengths (e.g., 735 nm and 405 nm). The peak intensity ratio Y/X is defined as the Raman signal intensity ratio between the peaks, i.e., the height ratio between the peaks. However, in the presence of an overlapping signal derived from another compound as a background in the range concerned, peak separation is performed to separate the peak concerned. Then, background intensity is subtracted from the height of this peak, and the results are regarded as the peak intensity concerned.

The invention claimed is:

1. A composition for catalyst production which is used in the production of a catalyst for gas phase catalytic oxidation reaction or a catalyst for gas phase catalytic ammoxidation reaction, wherein the composition for catalyst production is an aqueous solution comprising a niobium compound and hydrogen peroxide and optionally comprising an organic acid, a molar ratio (organic acid/Nb) of a concentration of the organic acid to a Nb concentration in the composition for catalyst production is 0.00 or more and 2.00 or less, a molar ratio (hydrogen peroxide/Nb) of a concentration of the hydrogen peroxide to a Nb concentration in the composition for catalyst production is 0.01 or more and 50 or less, and in a Raman spectrum of the composition for catalyst production by Raman spectroscopy, a ratio (Y/X) of an intensity Y of a largest peak observed in a range of 890 $cm^{-1}$ or more and 1000 $cm^{-1}$ or less to an intensity X of a largest peak observed in a range of 500 $cm^{-1}$ or more and 650 $cm^{-1}$ or less is 0 or more and 1.0 or less.

2. The composition for catalyst production according to claim 1, wherein the organic acid is one or more carboxylic acid compounds selected from the group consisting of dicarboxylic acid, dicarboxylic anhydride, dicarboxylic acid hydrate, and oxycarboxylic acid.

3. The composition for catalyst production according to claim 1, wherein in a Raman spectrum of the composition for catalyst production by Raman spectroscopy, a peak is present in a range of 685 $cm^{-1}$ or more and 785 $cm^{-1}$ or less.

4. A composition for catalyst production which is used in the production of a catalyst for gas phase catalytic oxidation reaction or a catalyst for gas phase catalytic ammoxidation reaction, wherein the composition for catalyst production is an aqueous solution comprising a niobium compound and hydrogen peroxide and optionally comprising an organic acid, and in a Raman spectrum of the composition for catalyst production by Raman spectroscopy, a ratio (Y/X) of an intensity Y of a largest peak observed in a range of 890 $cm^{-1}$ or more and 1000 $cm^{-1}$ or less to an intensity X of a largest peak observed in a range of 500 $cm^{-1}$ or more and 650 $cm^{-1}$ or less is 0 or more and 1.0 or less.

5. The composition for catalyst production according to claim 4, wherein a molar ratio (organic acid/Nb) of a concentration of the organic acid to a Nb concentration in the composition for catalyst production is 0.00 or more and 2.00 or less, and a molar ratio (hydrogen peroxide/Nb) of a concentration of the hydrogen peroxide to a Nb concentration in the composition for catalyst production is 0.01 or more and 50 or less.

6. A method for producing the composition according to claim 1, comprising:

a mixing step of mixing a solid niobium starting material and hydrogen peroxide water to prepare a dispersion of the solid niobium starting material; and a dissolution step of dissolving the solid niobium starting material in the dispersion of the solid niobium starting material to prepare a niobium compound-containing aqueous solution, wherein a molar ratio (hydrogen peroxide/Nb) of a concentration of hydrogen peroxide to a Nb concentration of the niobium compound in the niobium compound-containing aqueous solution is 0.01 or more and 50 or less, and a temperature of the dissolution step is 40° C. or higher and 70° C. or lower.

7. The method for producing a composition for catalyst production according to claim 6, wherein in the mixing step, an organic acid is further mixed, and a molar ratio (organic acid/Nb) of a concentration of the organic acid to a Nb concentration of the niobium compound in the niobium compound-containing aqueous solution is 0.00 or more and 2.00 or less.

8. The method for producing a composition for catalyst production according to claim 6, wherein the solid niobium starting material contains niobic acid.

9. The method for producing a composition for catalyst production according to claim 7, wherein the organic acid includes one or more carboxylic acid compounds selected from the group consisting of dicarboxylic acid, dicarboxylic anhydride, dicarboxylic acid hydrate, and oxycarboxylic acid.

* * * * *